(12) United States Patent
Leither et al.

(10) Patent No.: US 11,622,778 B2
(45) Date of Patent: Apr. 11, 2023

(54) ORTHOPEDIC DRILL GUIDE SYSTEM WITH LATERAL EDGE GUIDANCE, AND METHOD OF SURGERY FOR USE THEREWITH

(71) Applicant: ORTHO SOLUTIONS HOLDINGS LIMITED, Littleton, CO (US)

(72) Inventors: Andrew Leither, Akron, OH (US); Dustin Ducharme, Littleton, CO (US)

(73) Assignee: ORTHO SOLUTIONS HOLDINGS LIMITED, Littleton, CO (US)

(*) Notice: Subject to any disclaimer, the term of this patent is extended or adjusted under 35 U.S.C. 154(b) by 34 days.

(21) Appl. No.: 17/386,971

(22) Filed: Jul. 28, 2021

(65) Prior Publication Data

US 2022/0031339 A1 Feb. 3, 2022

Related U.S. Application Data

(60) Provisional application No. 63/059,439, filed on Jul. 31, 2020.

(51) Int. Cl.
*A61B 17/17* (2006.01)
*A61B 17/80* (2006.01)

(52) U.S. Cl.
CPC ................. *A61B 17/1728* (2013.01)

(58) Field of Classification Search
CPC ............ A61B 17/1728; A61B 17/1775; A61B 17/1725; A61B 17/17; A61B 17/808; A61B 17/8061; A61B 17/1782
See application file for complete search history.

(56) References Cited

U.S. PATENT DOCUMENTS

| | | | | |
|---|---|---|---|---|
| 7,819,877 B2* | 10/2010 | Guzman | ............ | A61B 17/1703 606/86 B |
| 7,935,126 B2* | 5/2011 | Orbay | ................ | A61B 17/1728 606/280 |
| 9,198,677 B2* | 12/2015 | Fritzinger | .............. | A61B 17/80 |
| 9,421,103 B2 | 8/2016 | Jeng et al. | | |
| 9,936,995 B2* | 4/2018 | Dacosta | ............ | A61B 17/1775 |
| 2009/0177239 A1* | 7/2009 | Castro | .................. | A61B 17/808 606/86 R |
| 2014/0180348 A1 | 6/2014 | Thoren et al. | | |
| 2019/0015140 A1* | 1/2019 | Dacosta | ............ | A61B 17/1775 |
| 2019/0090925 A1* | 3/2019 | Detweiler | .......... | A61B 17/8076 |
| 2020/0015868 A1* | 1/2020 | Dacosta | ............ | A61B 17/1775 |
| 2022/0000496 A1* | 1/2022 | Dacosta | ............... | A61B 17/842 |

* cited by examiner

*Primary Examiner* — Kevin T Truong
*Assistant Examiner* — Tracy L Kamikawa
(74) *Attorney, Agent, or Firm* — Hudak, Shunk & Farine Co. LPA

(57) ABSTRACT

The invention comprises a medical implant system with implant having a fastener hole for a fastener and further including a fusion screw, positioned to avoid interference with the implant fastener. The medical implant system also includes a guide that is mounted in the fastener hole and from an edge of the implant which provides for defined adjustability for angulation, and optionally depth, to allow for placement of the fusion screw so as to avoid impingement with the implant and the fasteners that secure it in place. The invention also relates to a method of surgery using the system.

19 Claims, 28 Drawing Sheets

ORTHOPEDIC DRILL GUIDE SYSTEM WITH LATERAL EDGE GUIDANCE, AND METHOD OF SURGERY FOR USE THEREWITH

FIELD OF THE INVENTION

The present disclosure relates to an invention which involves an medical implant system which includes an implant having a fastener hole and including an implant fastener that extends through the implant fastener hole, and further including a fixation device, such as one or more fusion screw, that needs to be placed so as to avoid interference with the implant fastener. The medical implant system thus, further includes a guide for the placement of that fixation device where the guide provides for defined adjustability with respect to that placement, for example for angulation, and optionally depth, to allow for placement so as to avoid impingement with the implant and the fasteners that secure it in place. The invention also relates to a method of surgery that incorporates the use of the medical implant system. The guide is designed for use with an independent (i.e., out of plate) fusion screw, but could be used as well in a three dimensionally contoured implant design where the implant includes curving sections with angled fastener holes that accept fasteners at various angles.

BACKGROUND OF THE INVENTION

The field of orthopedics has an ever-increasing understanding of the role that an implant system can play in response to trauma and a lack of function in a joint system. This is true when the implant is used to hold a bone or bone segments following injury as in a Lisfranc injury or in response to a condition that is congenital or manifests over time, such as flat foot or bunions. Accordingly, the art has advanced in designing systems that allow for multiple planes of fixation. This is the case for orthopedic plates that have fasteners, such as locking screws which cooperate with the plate to be fixed at a given angle, In addition, these systems are now sometimes used with additional fixation devices, such as lag or compression screws that are used to hold compression at the site of an osteotomy or otherwise to promote fusion. Some advances even provide fixation devices that are implanted in totally different planes than the implant fasteners. In all of these instances, the area is often small and congested, leaving little room for placement of the lag screws without worry about interference with the implant fasteners. The present invention provides an implant system that incorporates a drill guide member that uses a recess, such as the fastener recess, in the implant as a first mount (location), and about which the drill guide can pivot, and uses a vertical edge of the implant, such as an internal slot or peripheral edge of the plate outline to further support the drill guide and to define the path about which it travels.

SUMMARY OF THE INVENTION

The invention relates to a surgical guide which is mounted on an implant, such as a plate, to permit a placement of one or more fastener or fixation devices, i.e. a screw, which avoids impingement with other fasteners used with the implant, and also that is at the optimal angle and/or depth to achieve a desired result. The guide advantageously uses a fastener hole in the implant to secure and mount a guide body where the guide body can be pivoted in relation to the fastener hole, and the guide further includes a rider member that uses a separate vertical support edge of the implant to further support the guide as well as to defines limits or preferential positions of the guide relative to the implant, and thereby to the underlying bone. In a preferred embodiment, the implant fastener hole includes a peripheral (i.e., away from the center) recess or counterbore which supports an annular boss member on the guide body to act as a plain bearing in the recess. This permits the guide body to pivot relative to the implant fastener hole and since the peripheral recess is necessarily relatively shallow, the rider acts to further support the guide on the implant, and to define the positions of the guide body. The support edge which cooperates with the rider can be a dedicated slot in the implant or it can be a peripheral edge of the implant which has an outline that is contoured to define a start and stop path for the rider to define the limits or even include intermediate stops to position the guide.

The system also relates to a method of surgery which includes the use of an implant system having an implant with a fastener hole that includes a recess that supports and guides a rotatable guide body portion of a fixation device guide, and where the fixation device guide further includes a cooperation with a peripheral edge of the implant to support the fixation device guide and optionally to further define at least one position of a cannula on the fixation device guide which determines a position for placement of a drilled hole for the fixation device.

An object of the present disclosure is therefore to provide an implant system for orthopedic repair, such as osteotomy and fusion, which improves upon the short-comings of the prior art by providing for stability and adjustability, and to provide novel systems and methods for immobilizing the bone segments and/or joints. The implant system is of particular use in the small bones, meaning in a human below the knee or elbow, although the concept could also find use in spinal or veterinary surgery. The system allows for the use of fasteners in an implant or independently thereof, at a defined angle relative to the implant, for example to avoid impingement with other fasteners, or at an optimal angle to allow for fusion across a bone/bone interface, or to align a fastener to a hole to allow for thread match between the implant and fastener.

Another object of the present disclosure is to provide novel systems and methods for immobilizing bones or bone segments in all conditions of bone quality or pathology, and to avoid the most congested areas of ligament and tendon involvement, and so as to result in reliable bone fusion

DETAILED DESCRIPTION OF THE INVENTION

Figure 1:
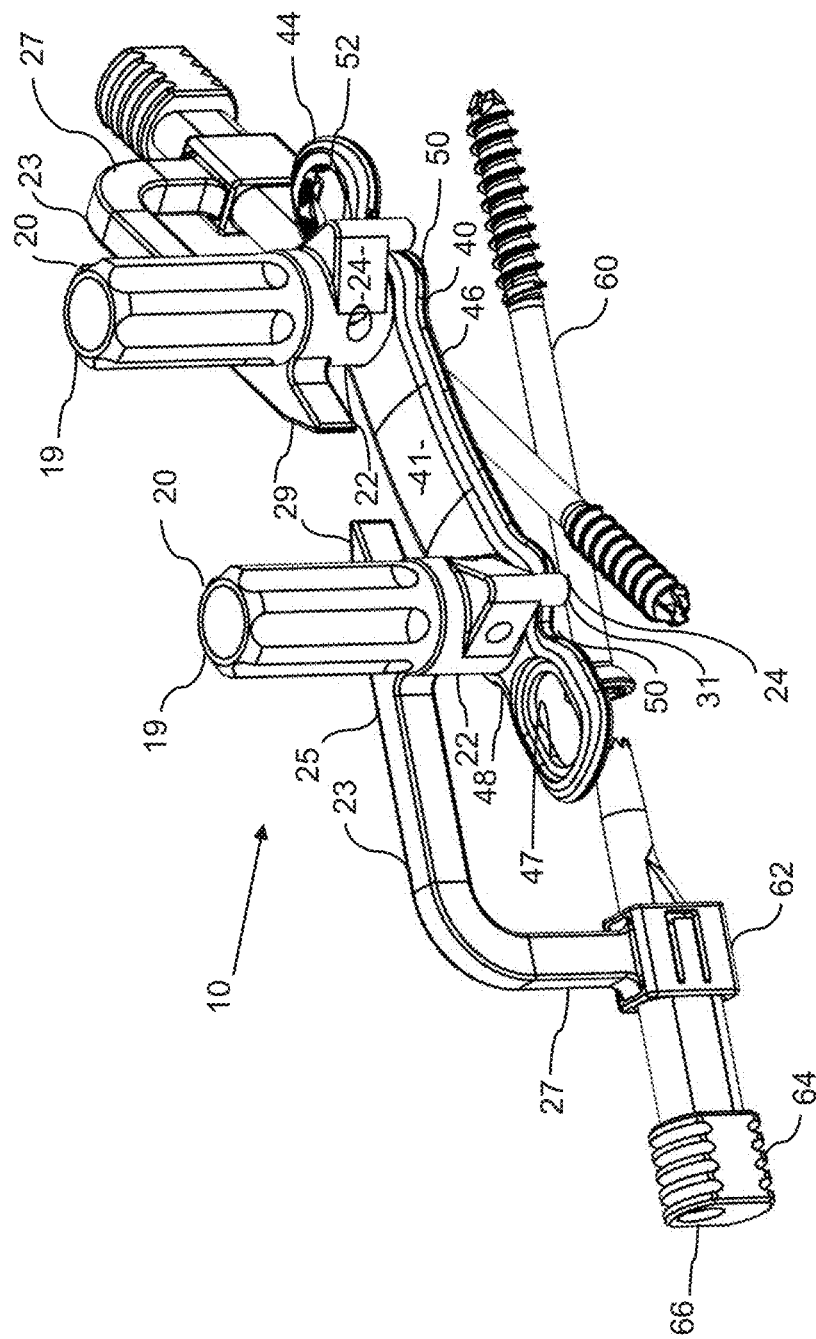
FIG. 1 is a top perspective view of the orthopedic drill guide system of the present invention including an implant plate with two drill guides in position to position two ancillary compression screws.
Figure 2:
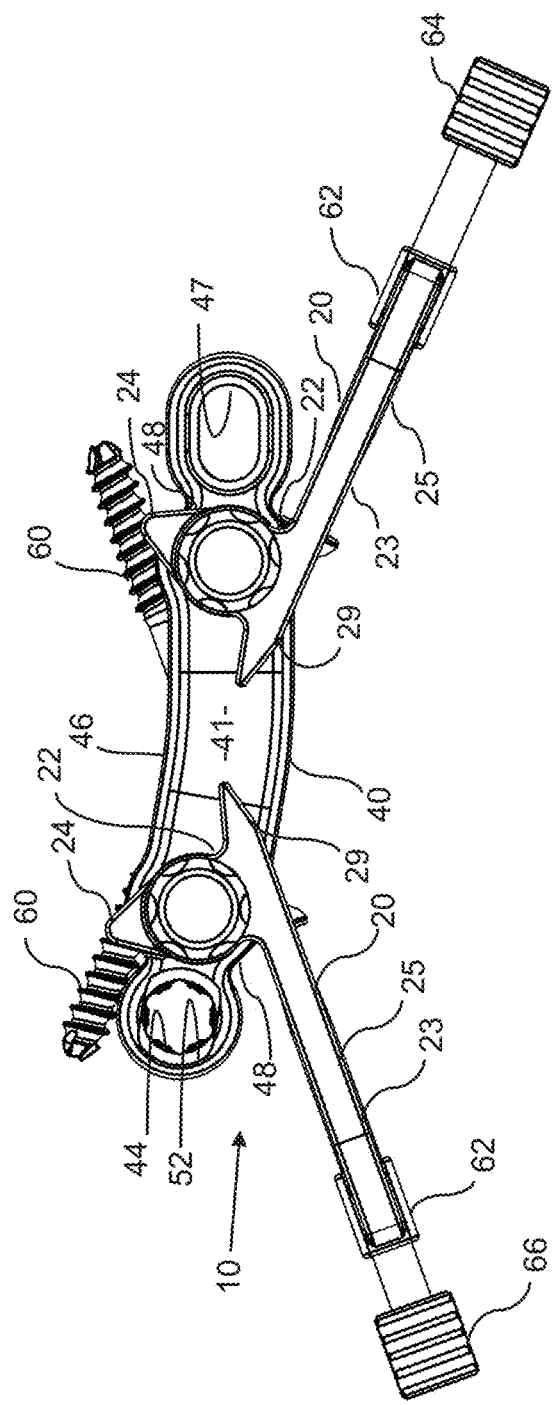
FIG. 2 is a top view of the orthopedic drill guide system of FIG. 1.
Figure 3:
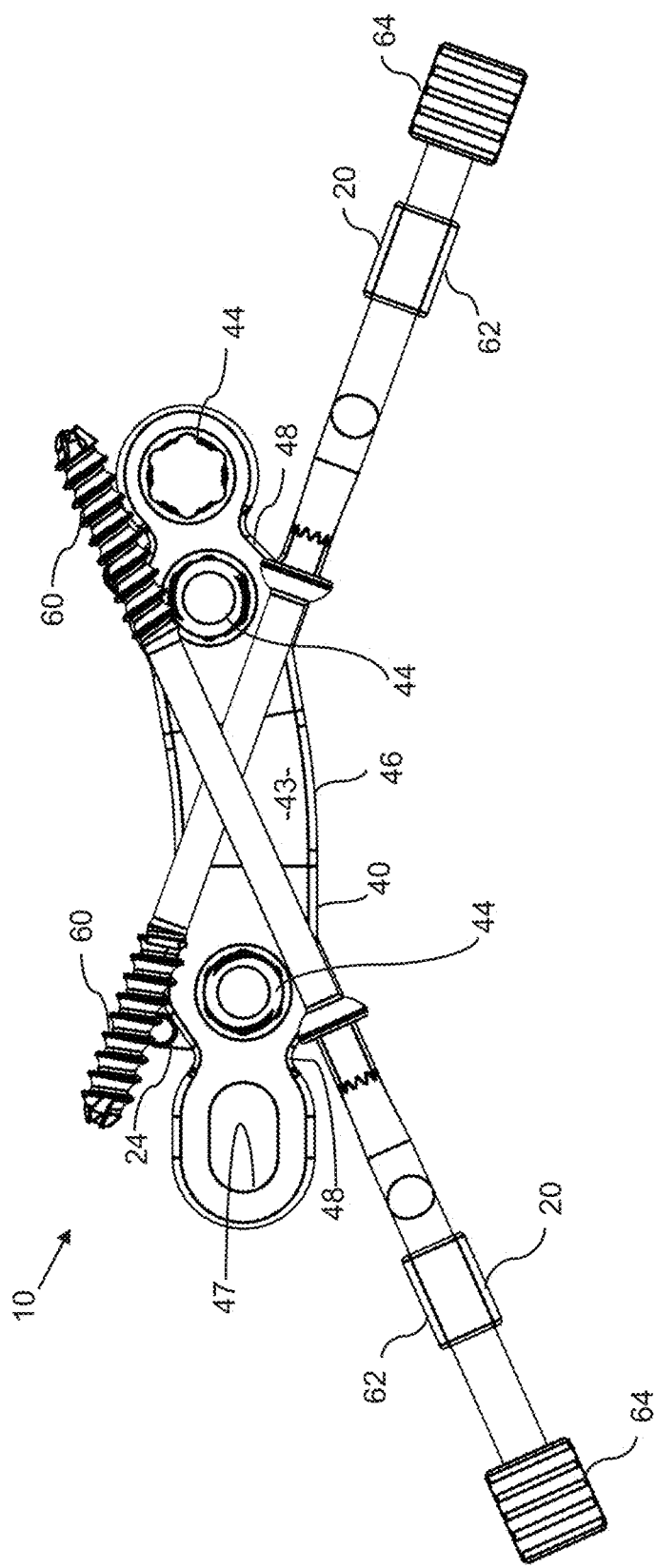
FIG. 3 is a bottom view of the orthopedic drill guide system of FIG. 1.
Figure 4:
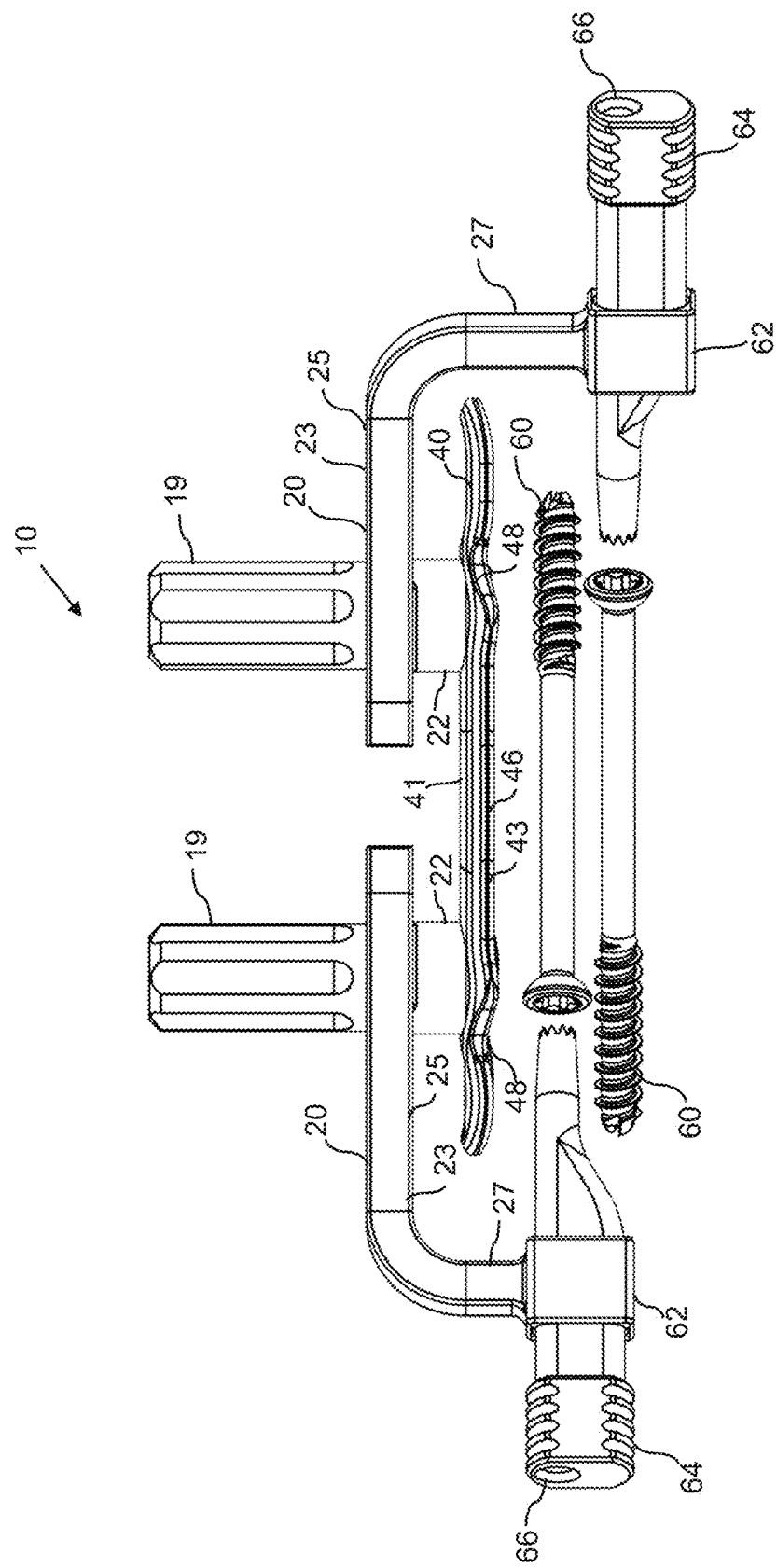
FIG. 4 is a first side view of the orthopedic drill guide system of FIG. 1 taken from the medial view (from an anatomical perspective)
Figure 5:
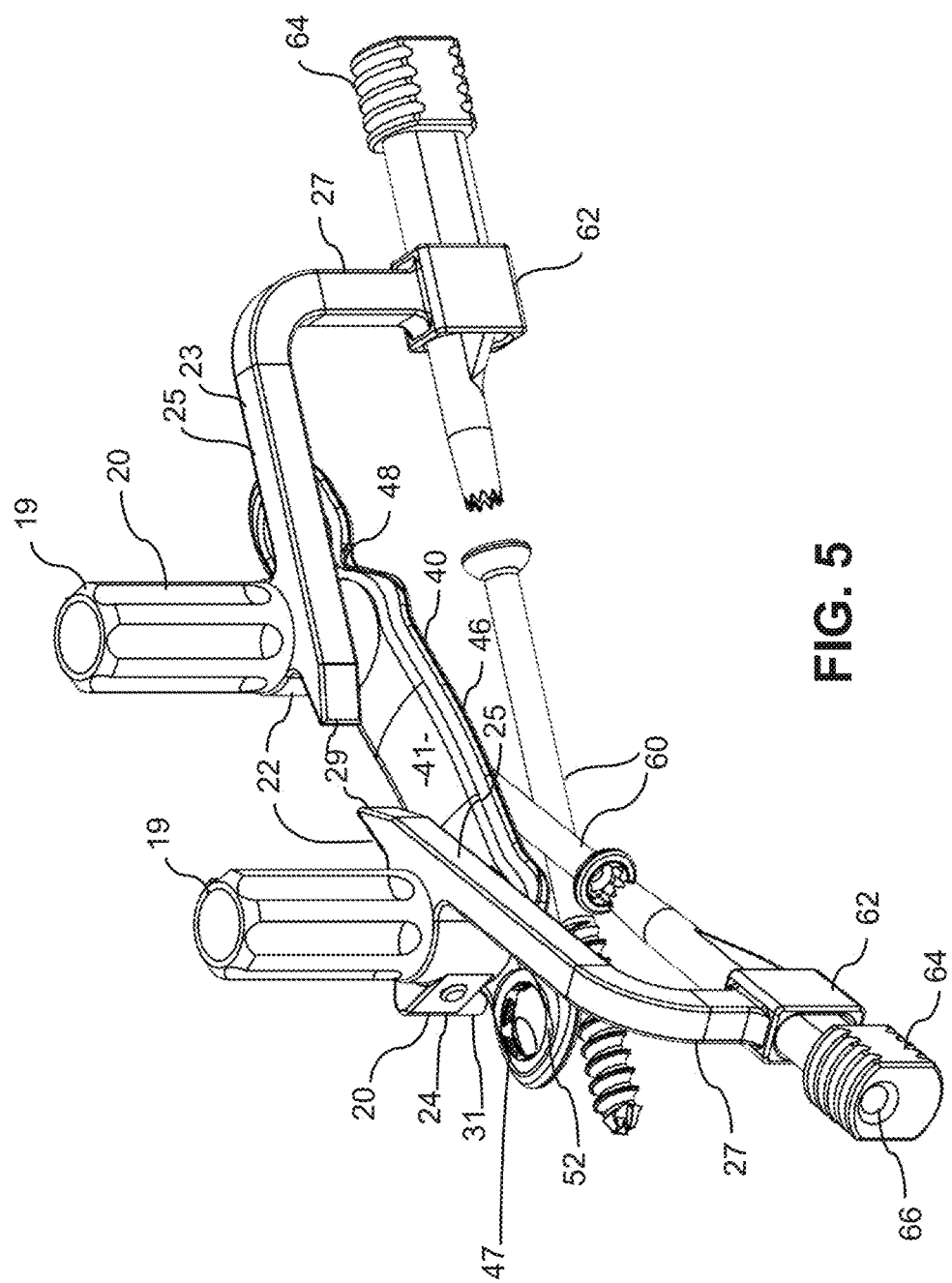
FIG. 5 is an end perspective view of the orthopedic drill guide system of FIG. 1 taken from the posterior end.
Figure 6:
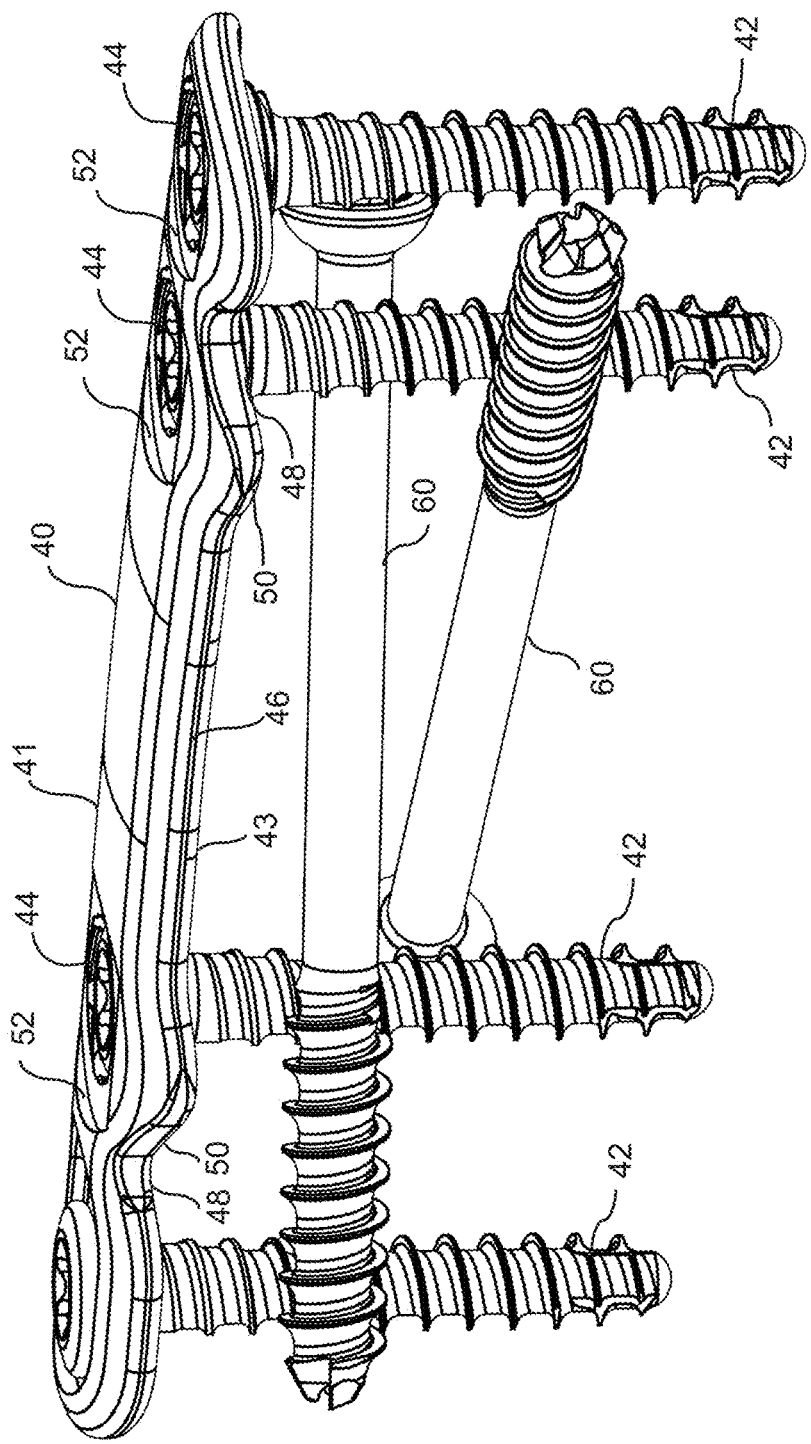
FIG. 6 is a second side view of the implant plate and screws of FIG. 1 with the fastener and ancillary screws in position.
Figure 7:
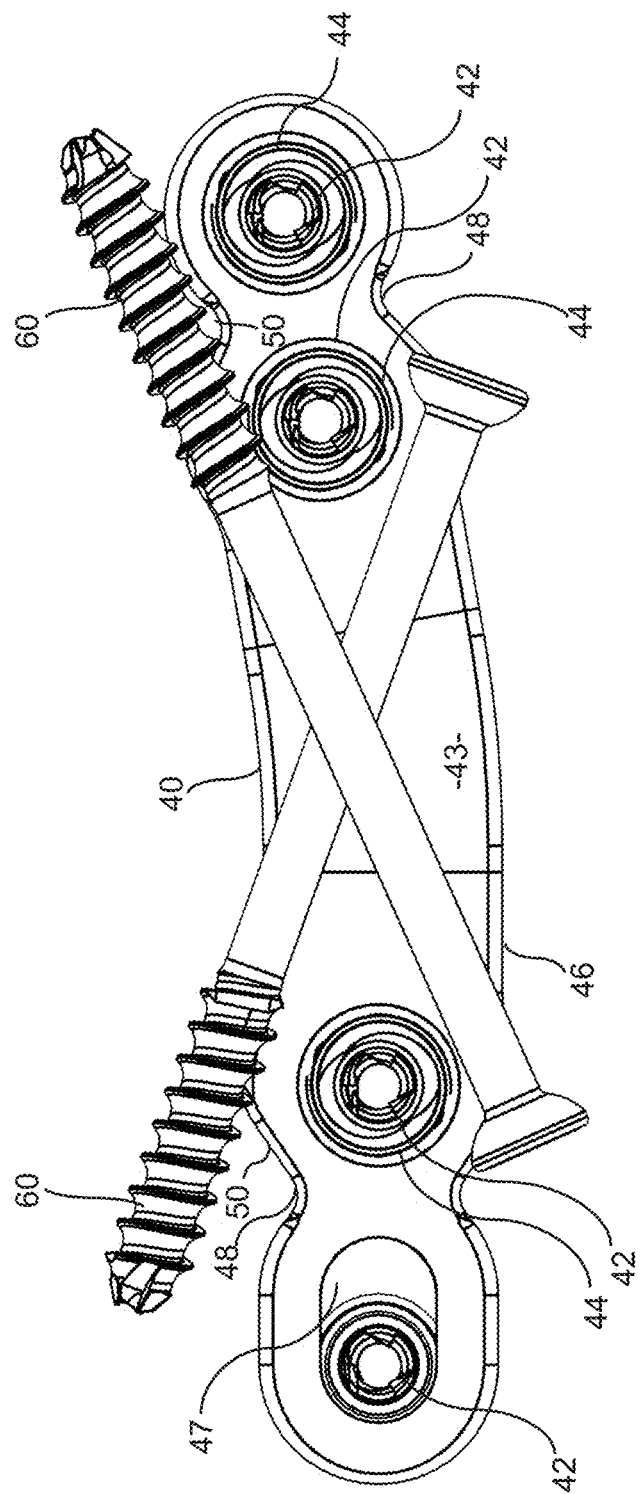
FIG. 7 is a bottom view of the implant plate of FIG. 6 with screws in position.
Figure 8:
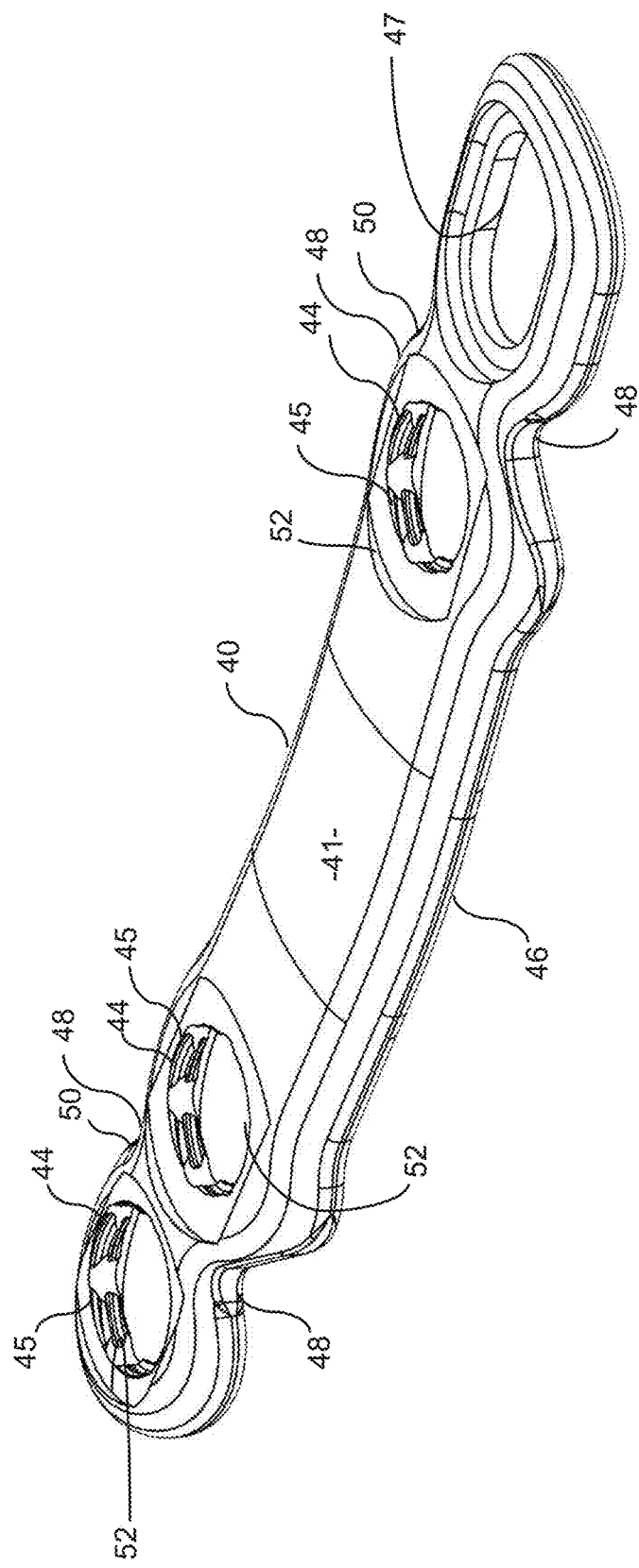
FIG. 8 is a top perspective view of the implant plate of the present invention without the fastener screws.
Figure 10:
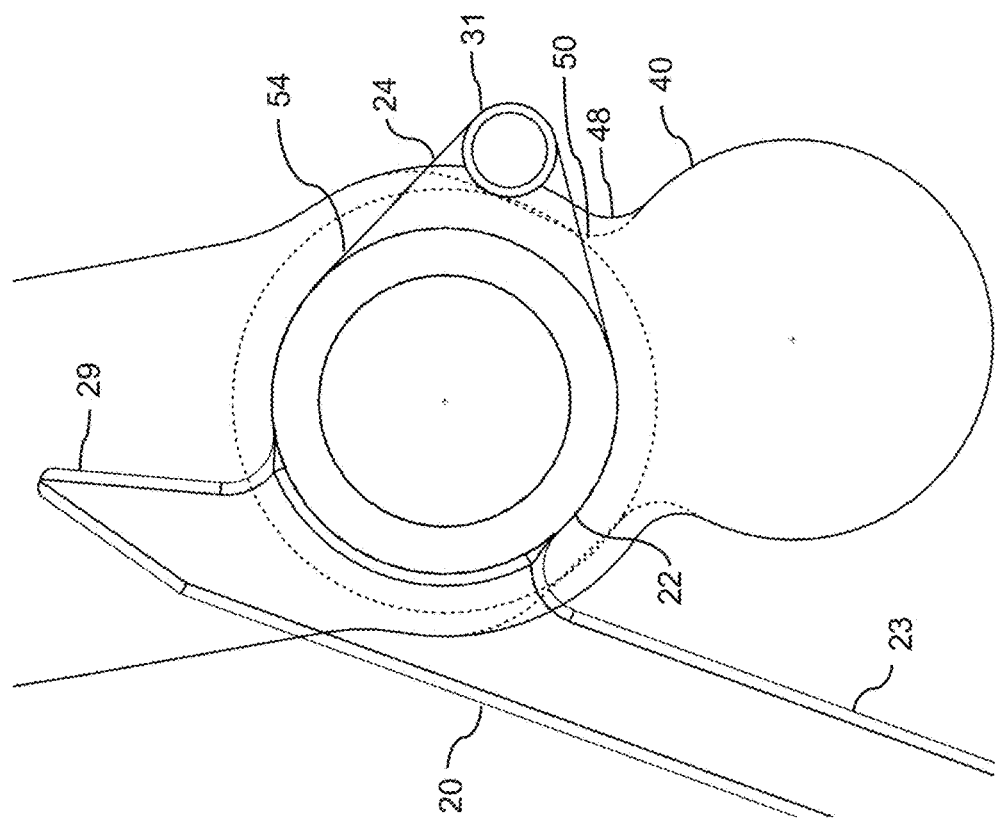
FIG. 10 is a top view of the rider of FIG. 9 in position on a specifically designed peripheral edge of the implant plate of the present invention.
Figure 9:
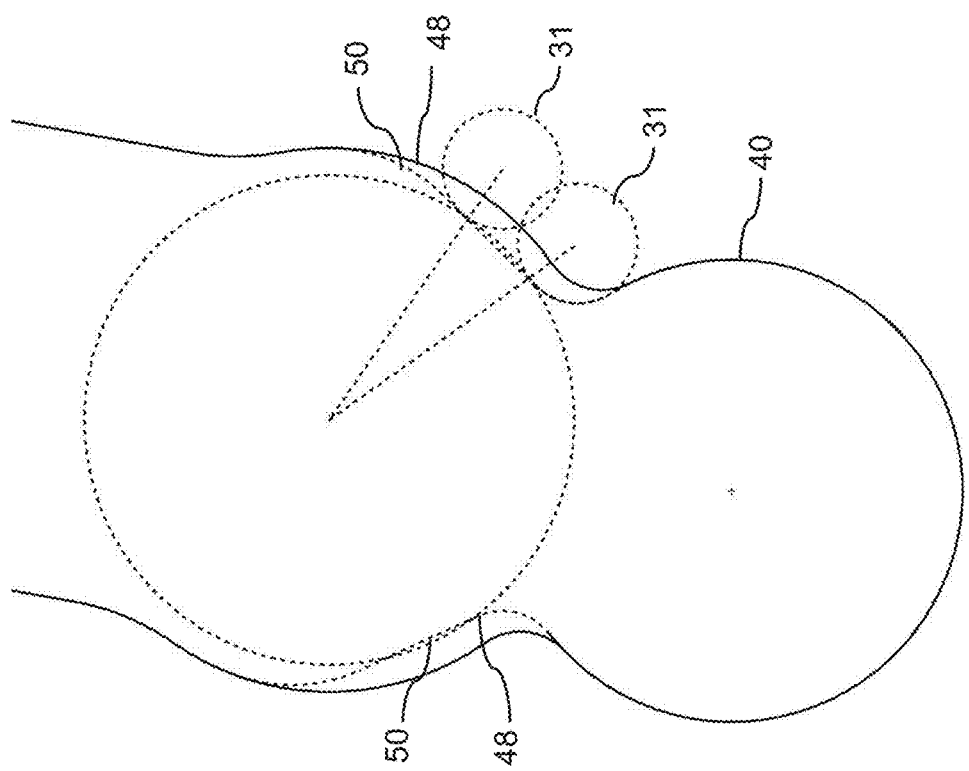
FIG. 9 is a top representation of the rider path of the drill guide of the present invention.
Figure 11:
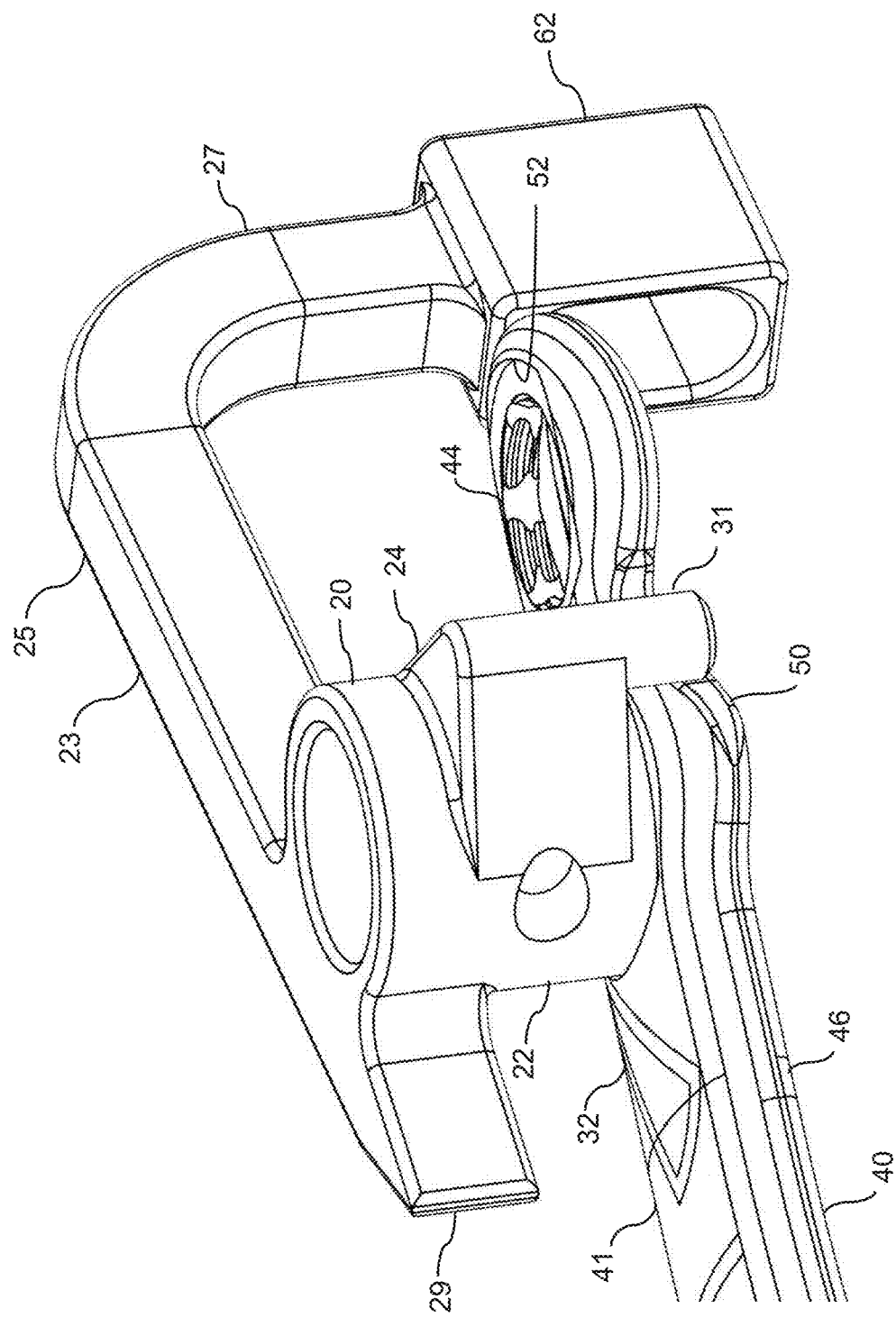
FIG. 11 is a second side view of the plate of FIG. 1 with the drill guide in place for use in positioning a fusion screw.
Figure 12:
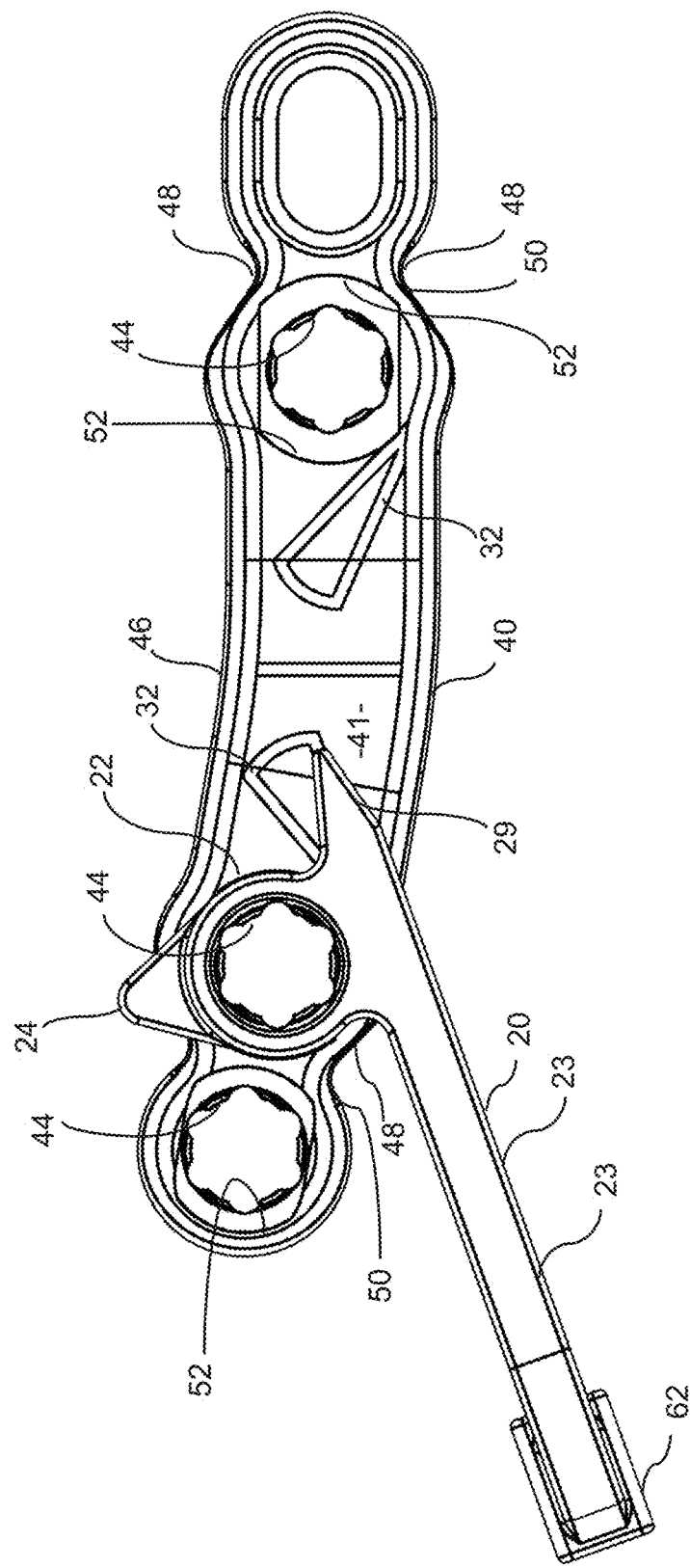
FIG. 12 is a top view of the implant plate and drill guide of FIG. 11 and illustrating the pivot insignia to indicate the hole placement.
Figure 13:
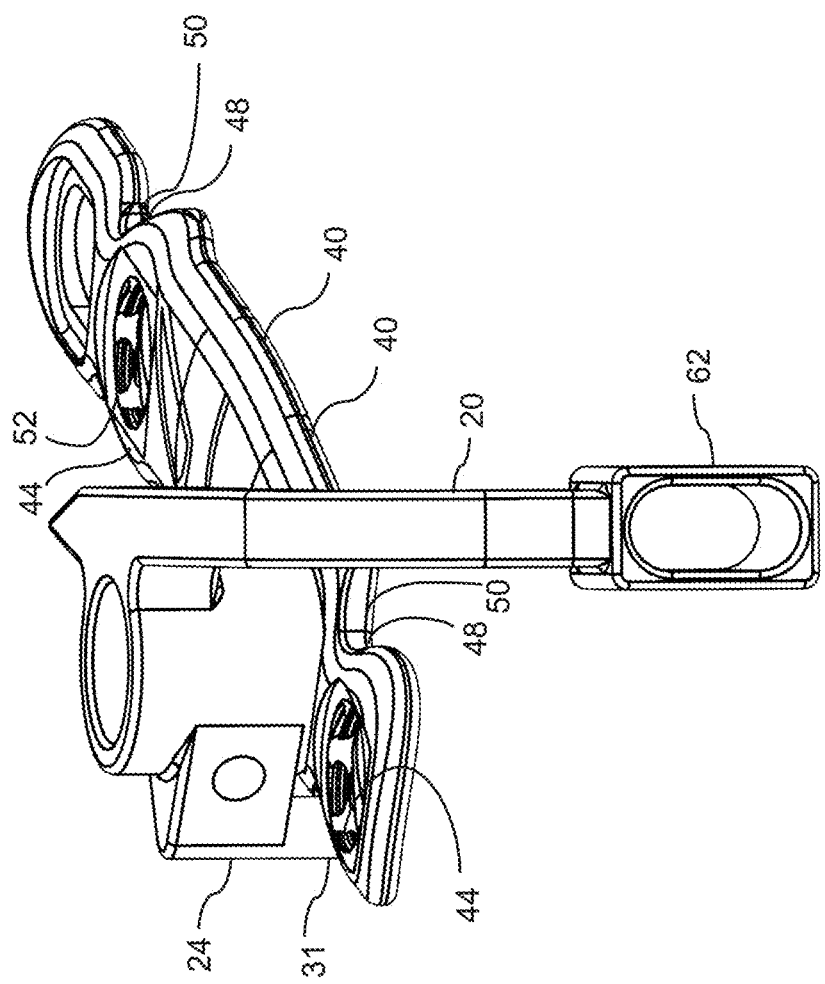
FIG. 13 is an end view of the implant and drill guide of FIG. 11 illustrating the arm and cannula housing.
Figure 14:
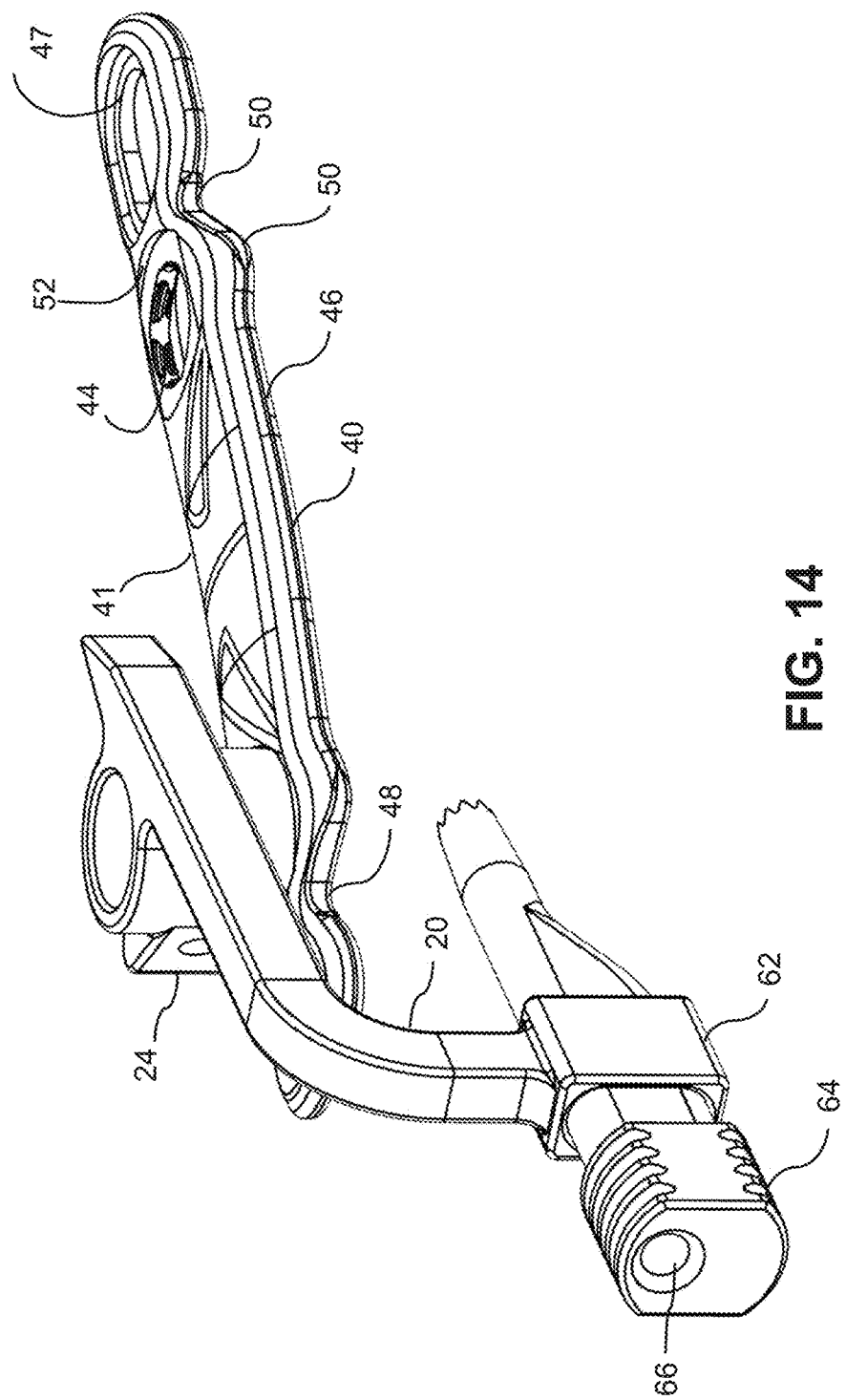
FIG. 14 is an end side perspective of the implant and drill guide of FIG. 11 including the cannula member in the cannula housing.
Figure 15:
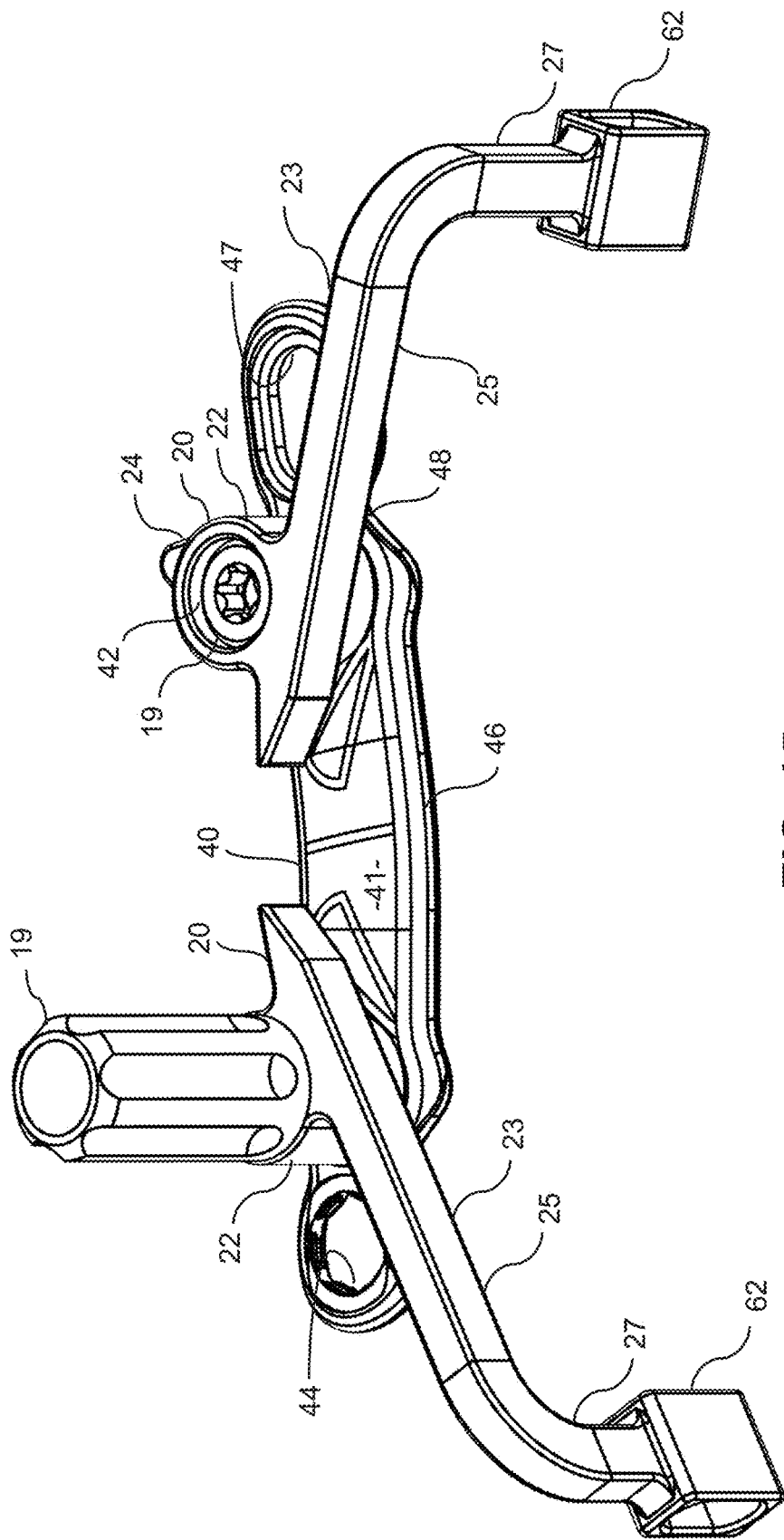
FIG. 15 is a top side view showing the invention with two drill guides in position on the implant plate of FIG. 1.

The present invention relates to an orthopedic drill guide system 10 including surgical drill guide 20 which is mounted on an implant 40, which is illustrated as a plate having fasteners 42 that are screws. The implant includes a top surface 41 which faces away from the bone, a bottom surface 43 which faces the bone, and a peripheral edge 46 along the through depth which will be referred to as "vertical" in relation to the top of bottom surface, although it does not have to be orthogonal. In addition, the implant system includes fixation devices 60 such as one or more compression screws which may be independent of the implant and its fasteners. The implant is further illustrated as including a compression slot 47 at one end, and the plate includes a rounded contour with necked portions 48 between fastener openings 44.

The system also includes one or more drill guides 20 to permit a placement of one or more of the fusion fastener or fixation devices 60, i.e., a screw, which avoids impingement with other fasteners used to secure the implant, and also that is at the optimal angle and/or depth to achieve a desired result. The guide 20 advantageously uses a hole in the implant, such as a fastener hole 44 to secure and mount a guide body 22 where the guide body 22 can act as a rotatable tether and can be pivoted in relation to the fastener hole 44. The guide body 22 can be secured in the fastener hole 44 by being journaled around a post member of a thumb screw or set screw 19 which is screwed into the fastener hole 44. The guide body includes an L-shaped arm 23 where the long side 25 is parallel to the long axis of the plate and the short side 27 is orthogonal to it, although it is envisioned that an angle of 75°-105° (90°±10 or 15°) can be used. The arm 23 includes a V-shaped extension 29 that acts as a pointer to indicate a position relative to a marker 32 on the plate upper surface 41 where the device allows for an angle of adjustment of from 5° to 45° (20°±10 or 15°).

The guide further includes a rider member 24 having an associated post 31 that uses a separate vertical relative to an outwardly facing surface support edge 50 of the implant to further support the guide as well as to defines limits or preferential positions of the guide relative to the implant, and thereby to the underlying bone. The fastener holes 44 of the implant include internal threads portions 45 which are interrupted to allow for variable angle locking with the implant fasteners. These threads can be used to hold the drill guide 20 in position by means of an associated thumb screw or set screw 19.

Figure 16:
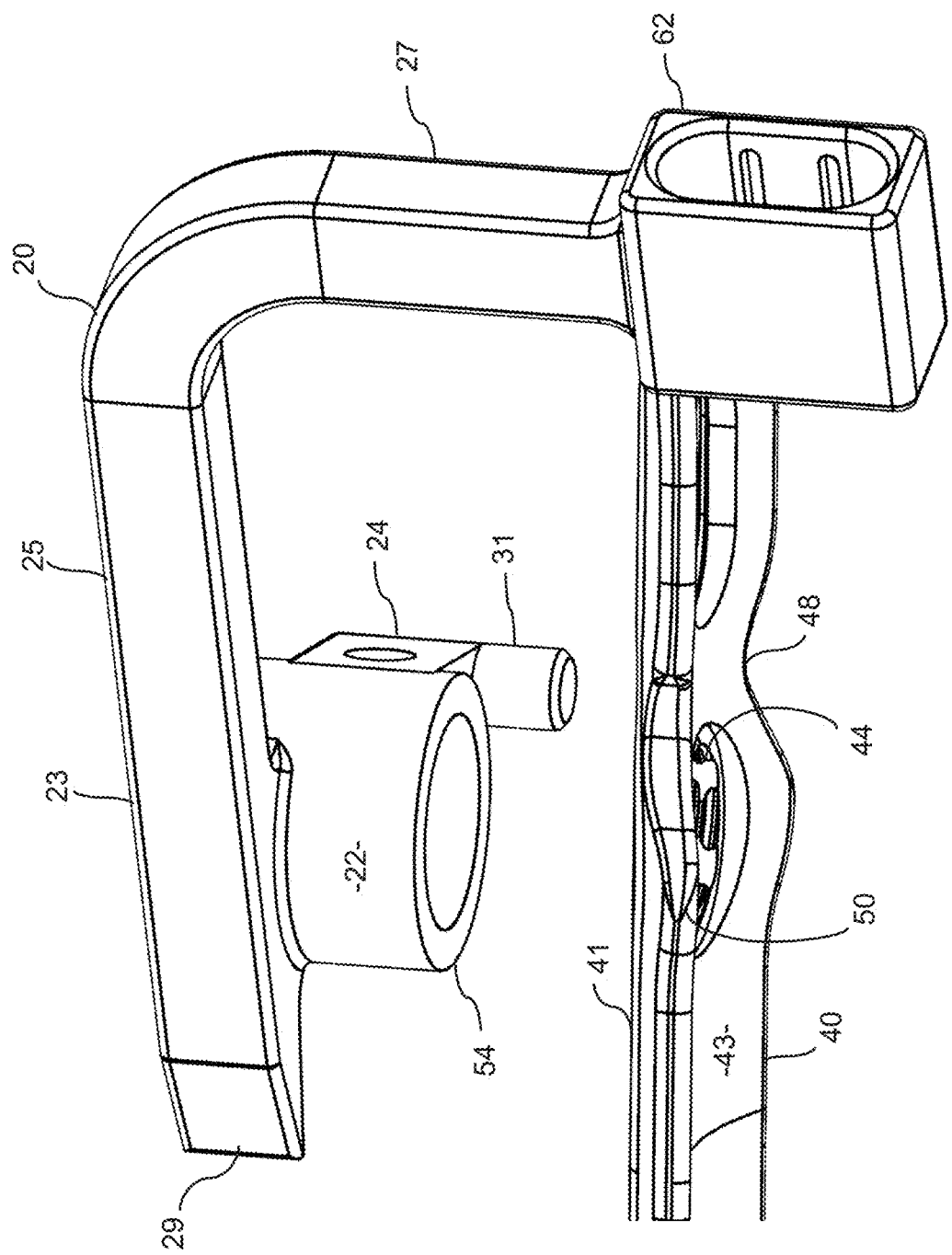
FIG. 16 is an exploded view of the implant and drill guide of FIG. 1 from the second side.
Figure 17:
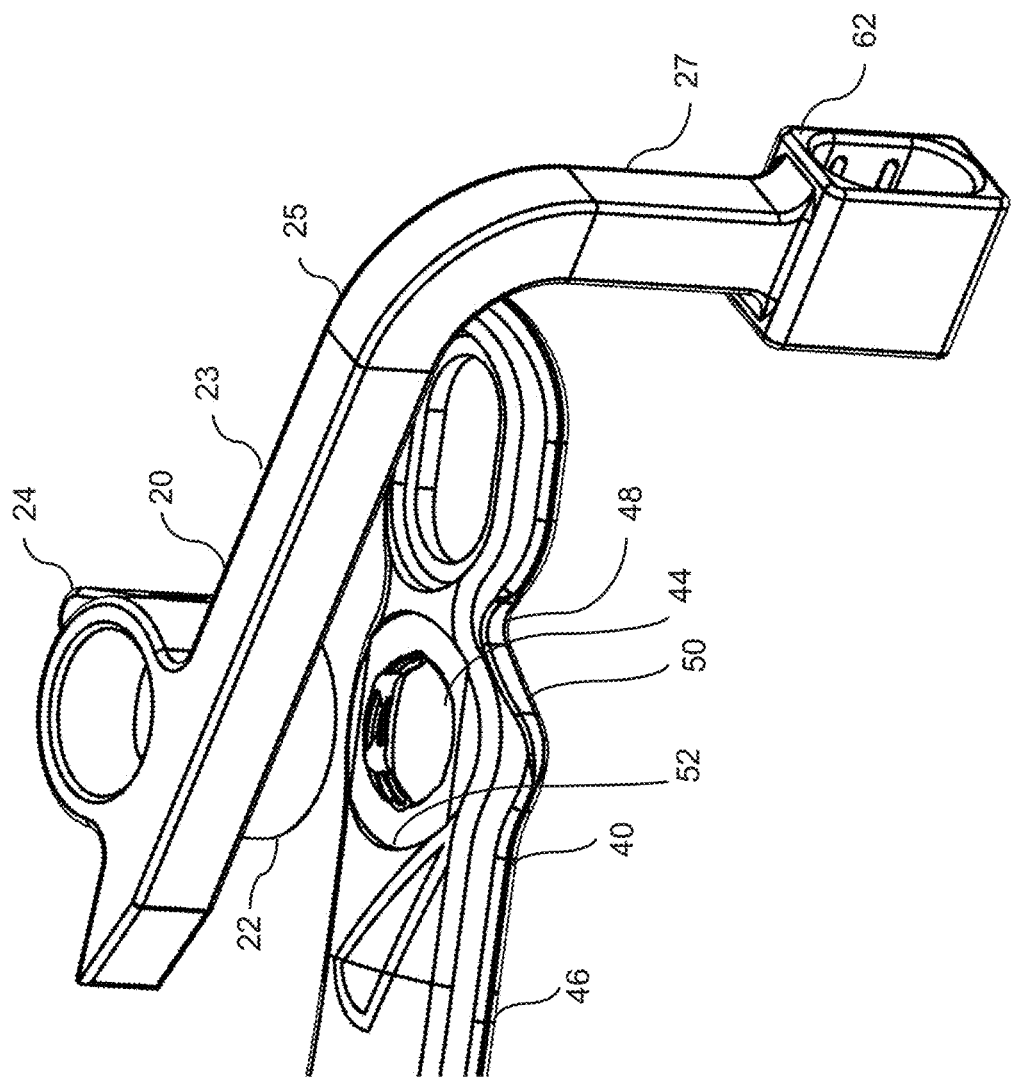
FIG. 17 is an exploded view of the implant and drill guide of FIG. 1 from the first side.
Figure 18:
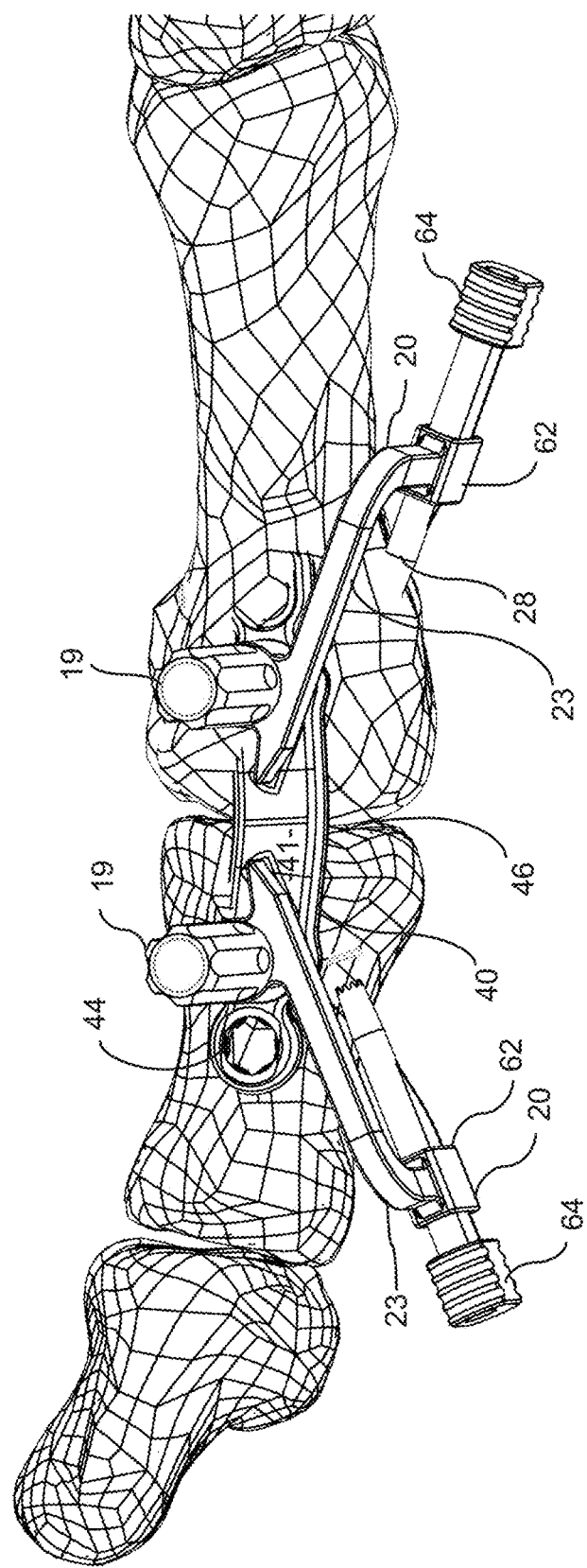
FIG. 18 is an illustration of the first step in use of the assembly of the parts of a drill guide in accordance with the present invention.
Figure 19:
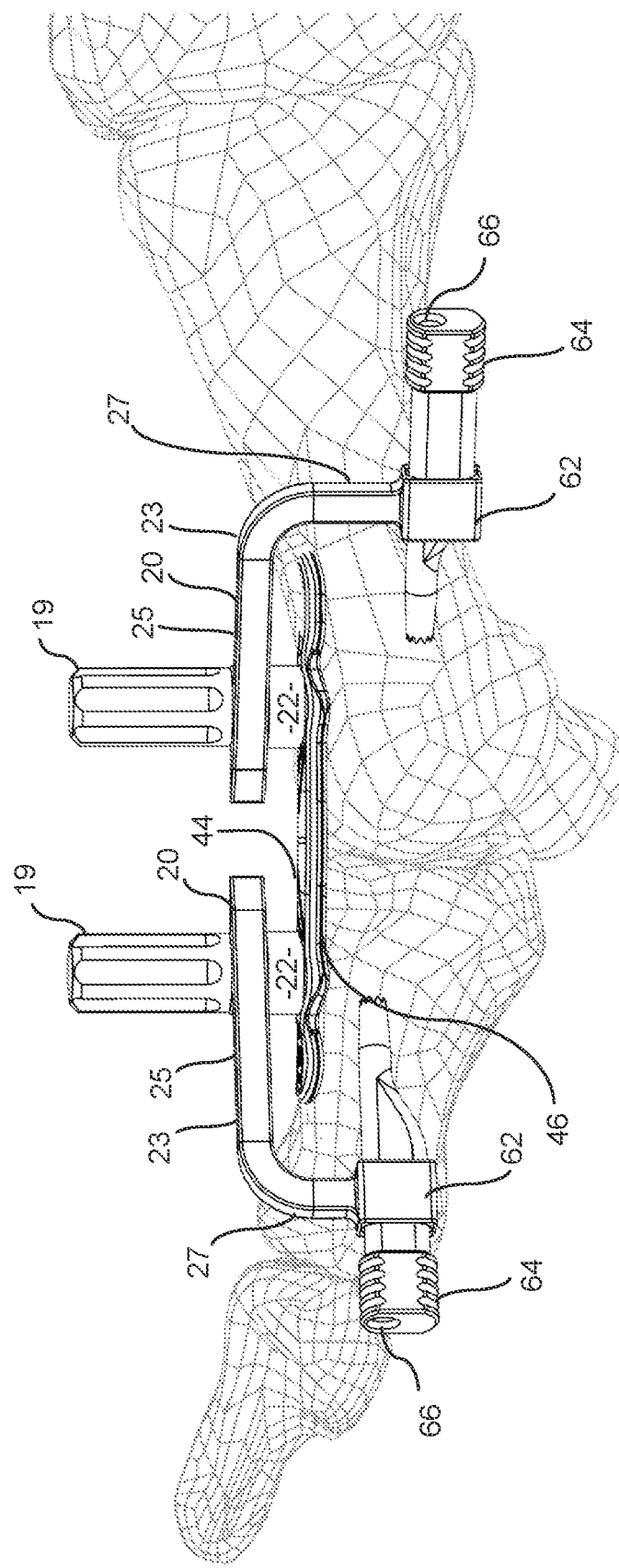
FIG. 19 is an illustration of the assembly of FIG. 18 from the medial side of the foot.
Figure 20:
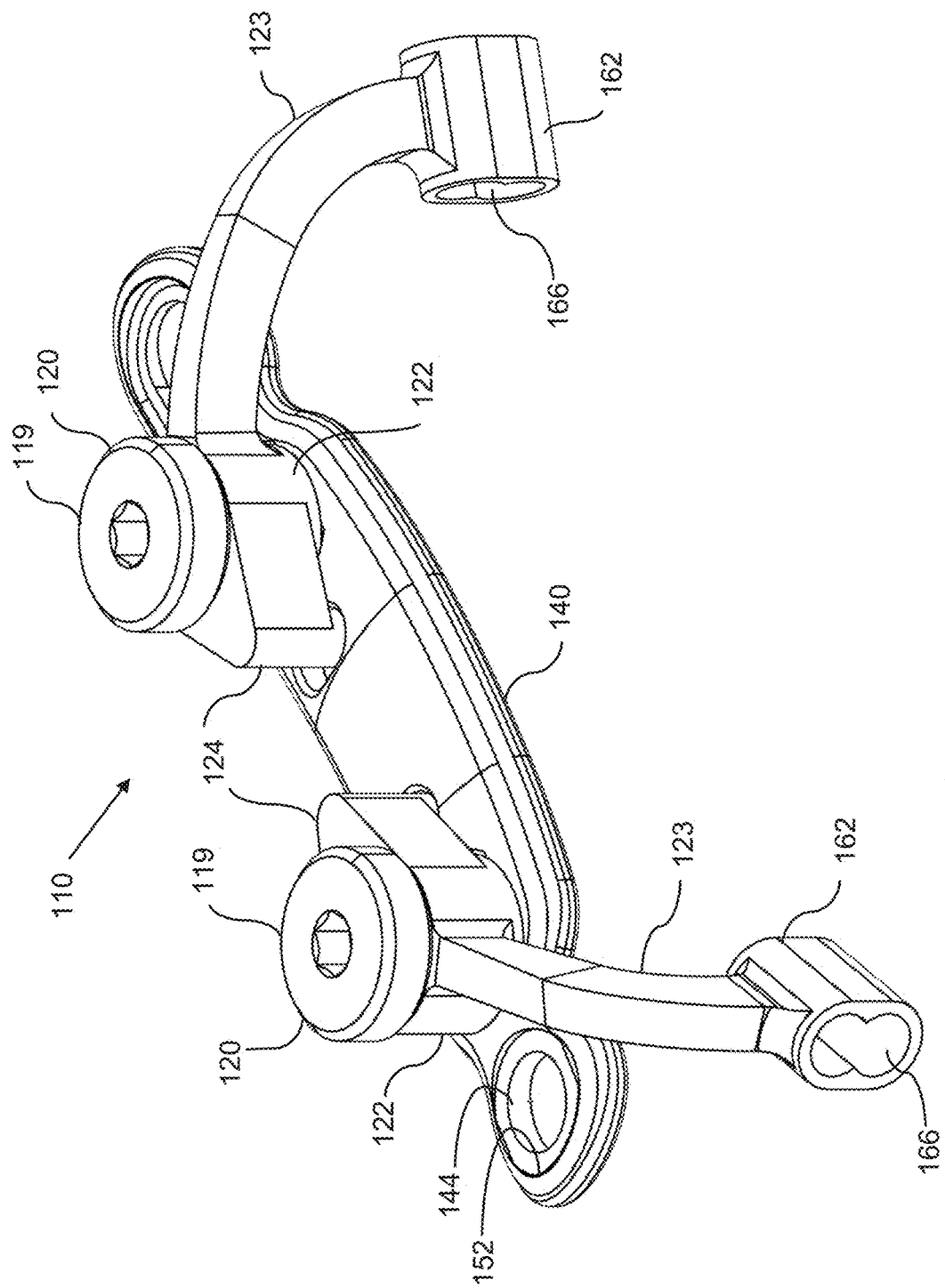
FIG. 20 is an illustration of a second embodiment of the orthopedic drill guide system of the present invention including an implant plate with two drill guides in position to position two ancillary compression screws and wherein the depth of the compression screws can be selected between an upper and lower position.
Figure 21:
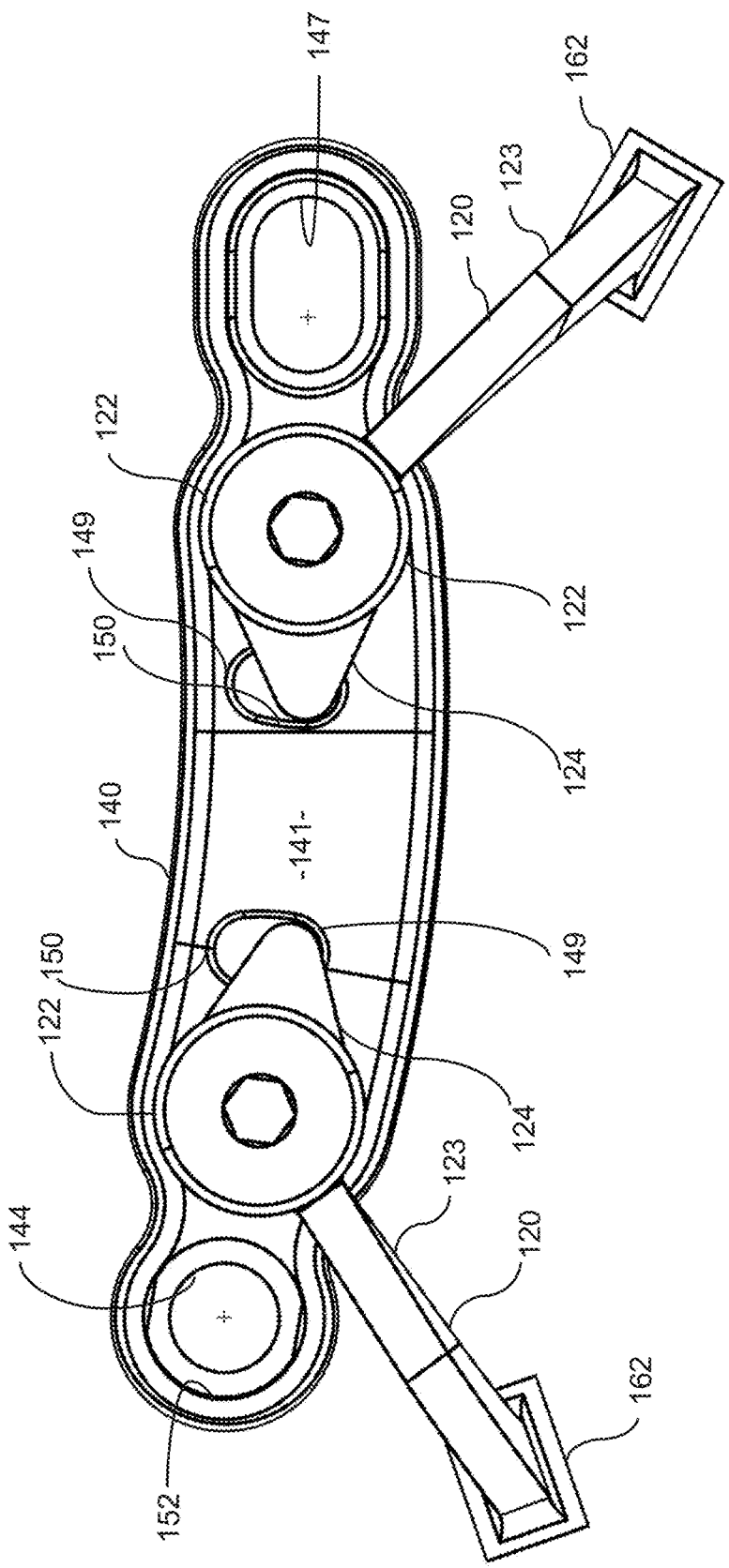
FIG. 21 is a top view of the assembly of FIG. 20.

In a preferred embodiment, the implant fastener holes 44 includes a peripheral (here meaning "radially outward of") recess or counterbore 52 which supports an annular boss member 54 (shown in FIG. 16) on the guide body 22 to act as a plain bearing in the recess 52. This permits the guide body 22 to pivot relative to the implant fastener hole 44 and since the peripheral recess is necessarily relatively shallow, the surface of the rider post 31 acts to further support the guide on the implant, and to define the positions of the guide body. The support edge 50 which cooperates with the rider can be a dedicated slot 150 in the implant as is shown in the second embodiment or it can be a peripheral edge 50 of the implant which has an outline that is contoured to define a start and stop path for the rider to define the limits or even include intermediate stops to position the guide.

The drill guide 20 further includes a cannula housing 62 which is an extension of the drill guide arm 23. The cannula housing 62 receives a cannula member 64 that includes a drill cannula 66. The cannula member includes an offset through hole 66 which can be positioned at a higher or lower position in the cannula housing such that a hole can be drilled in one of two levels relative to the plate.

Figure 23:
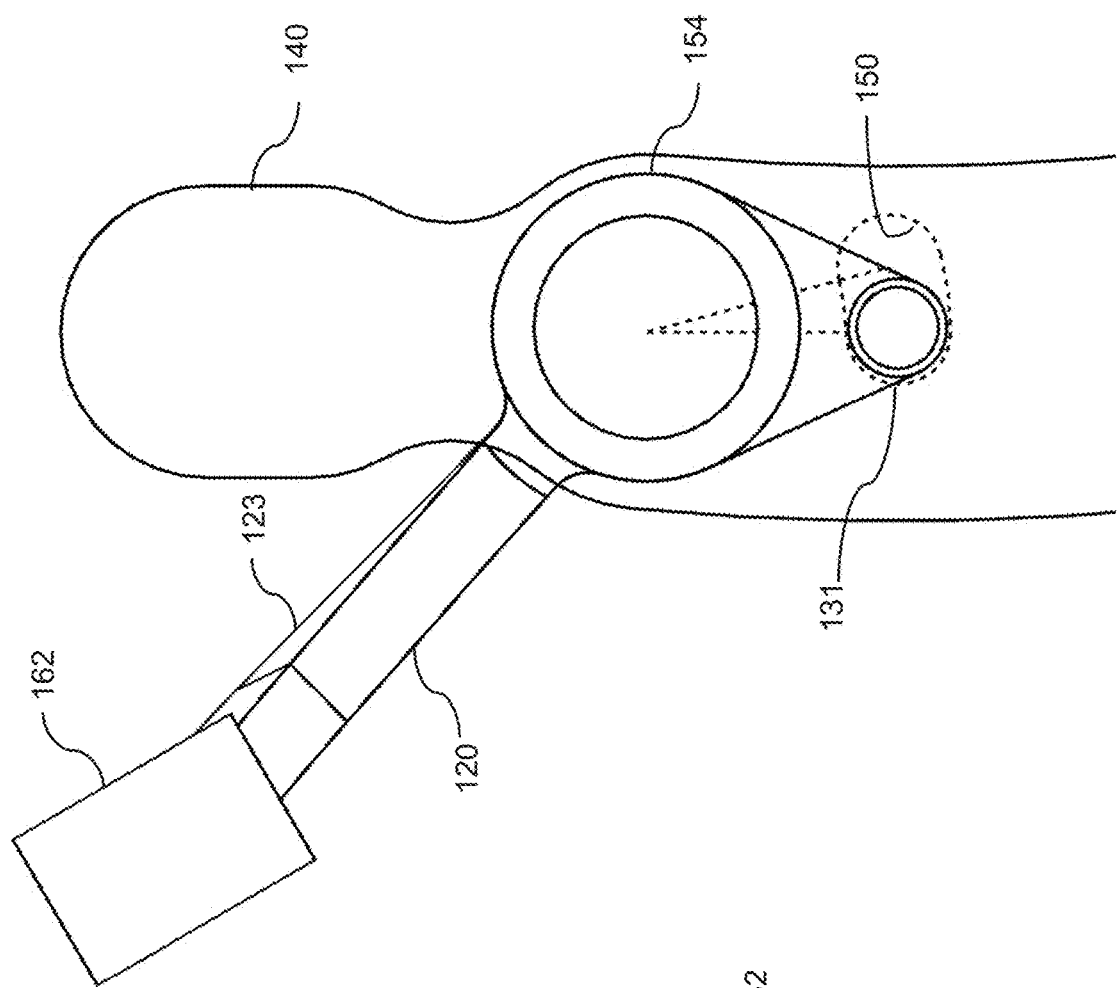
FIG. 23 a top illustration of the limits of adjustment of the drill guide system of FIG. 20 in accordance with the present invention.
Figure 22:
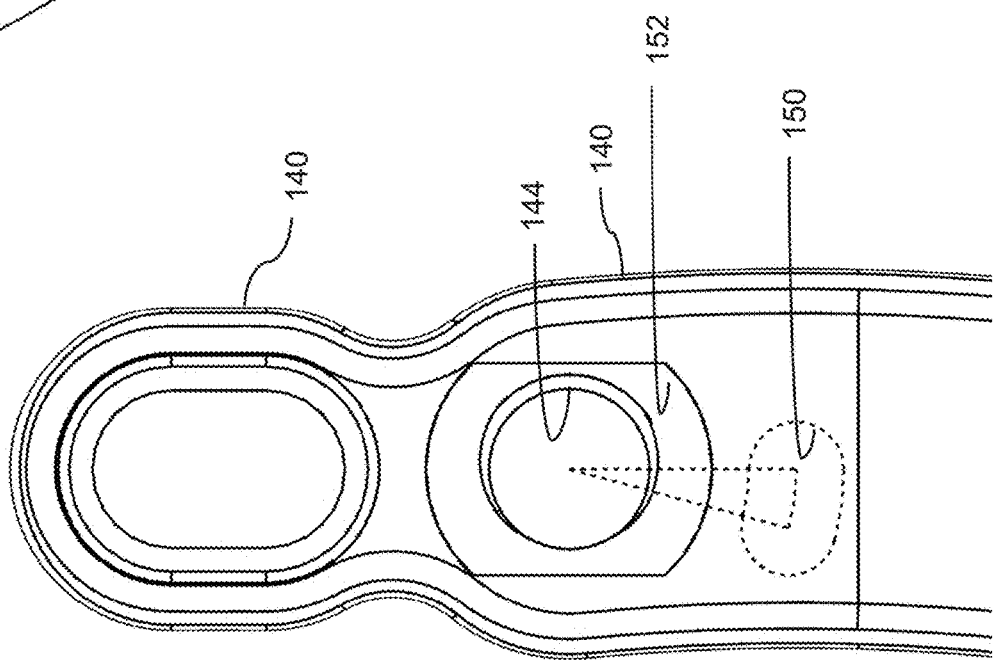
FIG. 22 is a top view of the implant plate of FIG. 20 illustrating the use of a vertical edge of a slot to define the limits of rotation of the drill guide body relative to a plate fastener hole.
Figure 24:
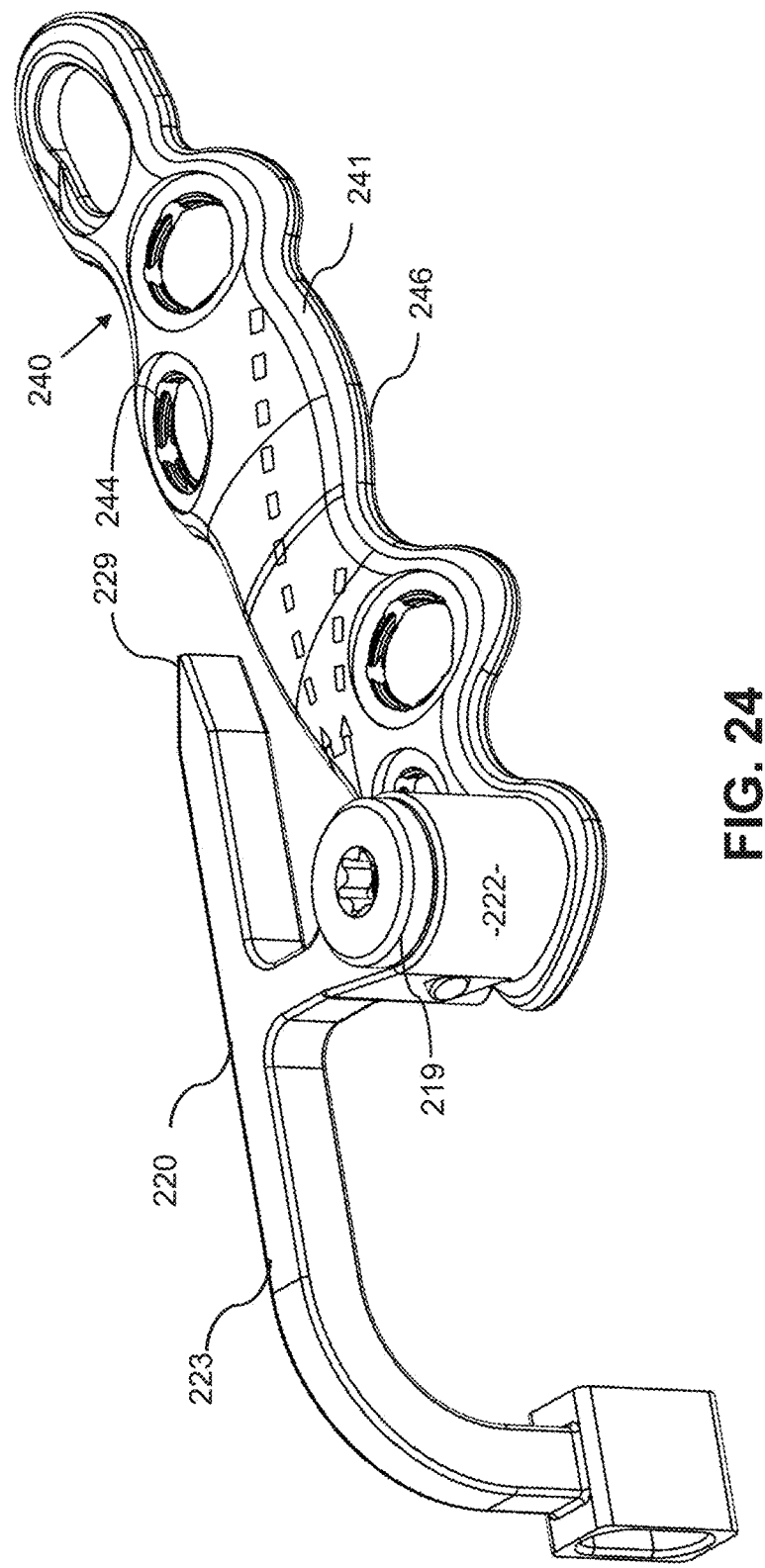
FIG. 24 is a top side view of a third embodiment of the implant drill guide system of the present invention.
Figure 25:
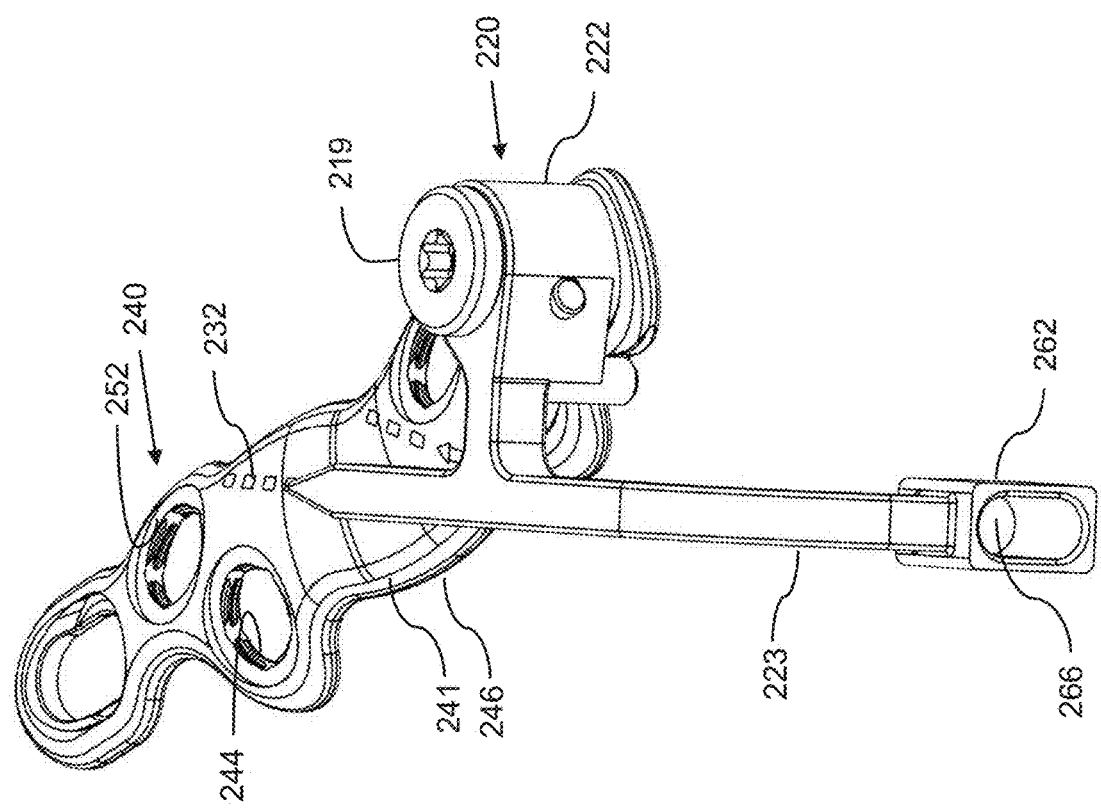
FIG. 25 is a top end view of the implant drill guide system of FIG. 24.
Figure 26:
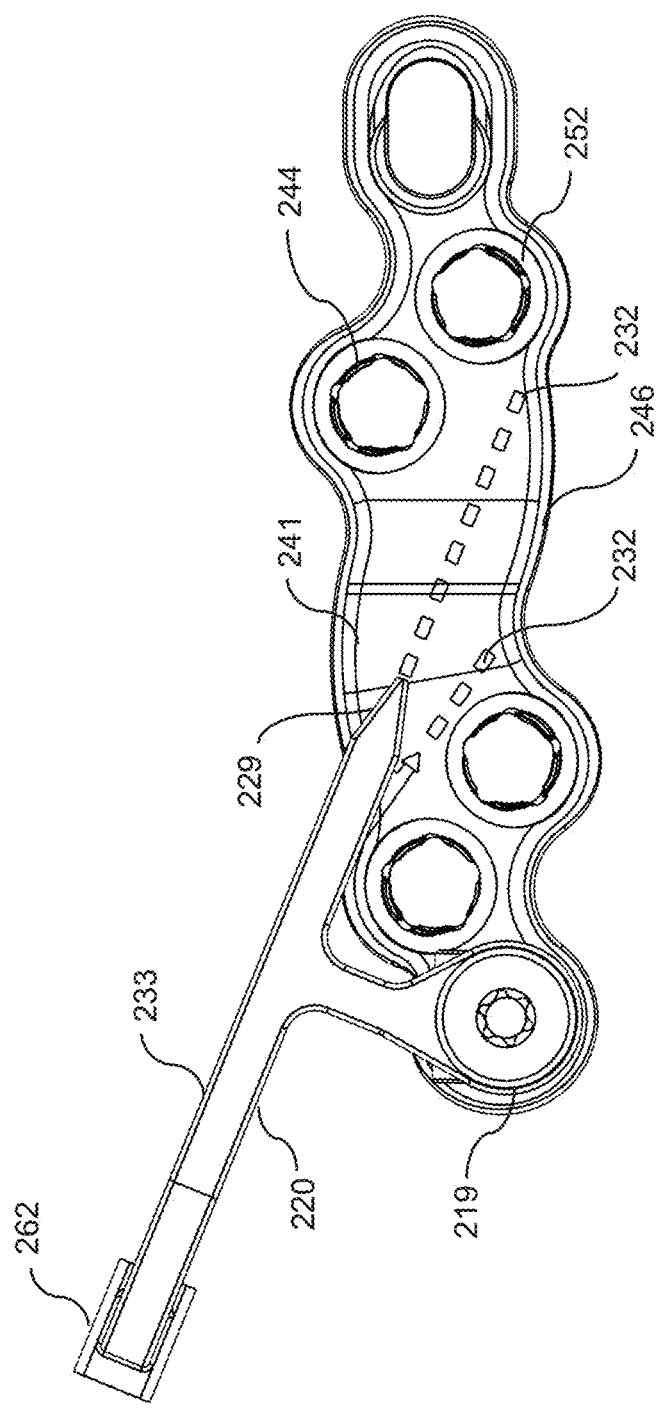
FIG. 26 is a top view of the implant drill guide system of the FIG. 24 with the drill guide in a first position on the implant.
Figure 27:
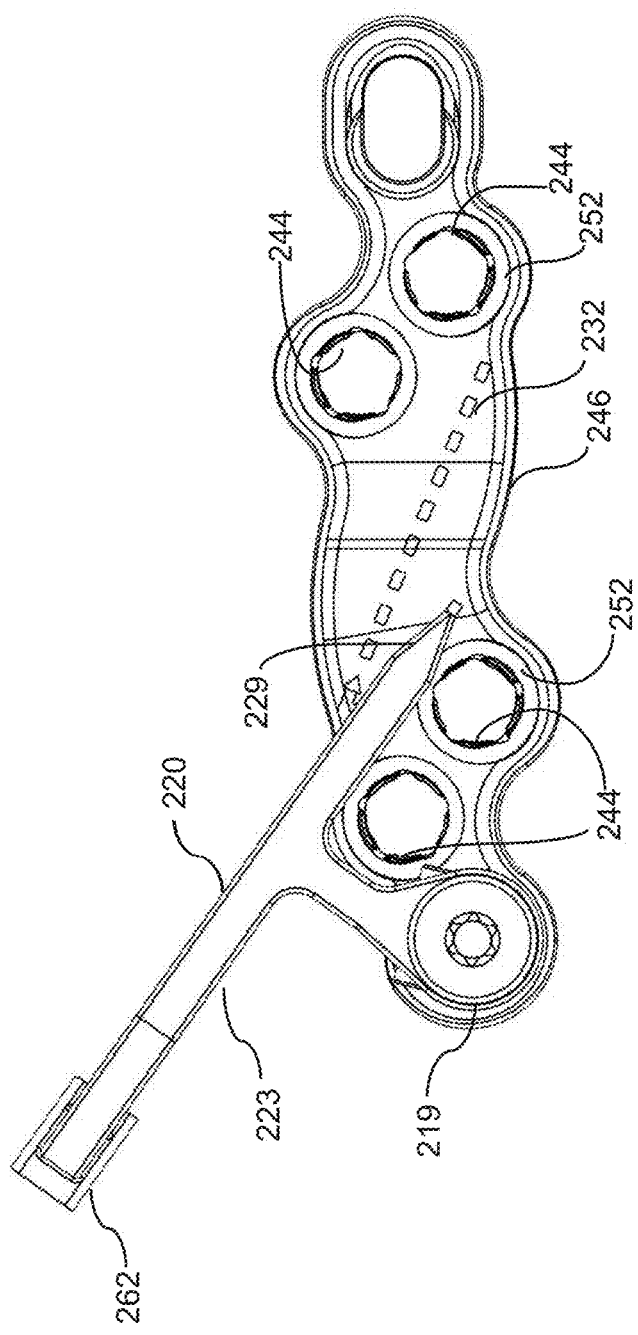
FIG. 27 is a top view of the implant drill guide system of FIG. 24 with the drill guide in a second position on the implant.
Figure 28:
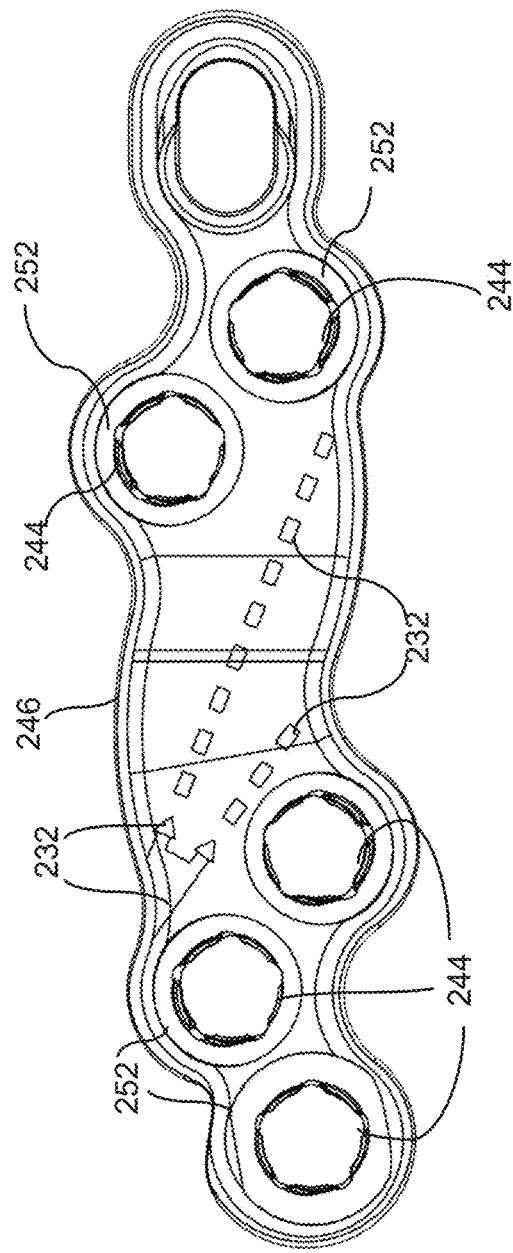
FIG. 28 is a top view of the implant of FIG. 24 showing the marked indicia for the selected positions of the drill guide.

A second embodiment of the invention is shown in FIGS. 20-23. In this embodiment, the implant 140 has a top surface 141 and a bottom surface 143 separated by an edge 146 and the top surface 141 includes a dedicated slot 149 that provides the vertical edge 150 for the post 131 of the drill guide rider 124. In this embodiment, the drill guide 120 has a drill guide body 122 with an arm 123 that carries the cannula housing 162 or which provides a two position drillway 166. The drill guide body 122 has an annular surface 154 which rotates in the counterbore 152 provided around a fastener recess 144. A set screw 119 secures the drill guide to the implant 140. FIGS. 22 and 23 illustrate the stable and controlled pivoting of the drill guide relative to the implant 140.

The system also relates to a method of surgery which includes the use of an implant system having an implant with a fastener hole that includes a recess that supports and guides a rotatable guide body portion of a fixation device guide, and where the fixation device guide further includes a cooperation with a peripheral edge of the implant to support the fixation device guide and optionally to further define at least one position of cannula on the fixation device guide which determines a position for placement of a drilled hole for the fixation device.

Figure 29:
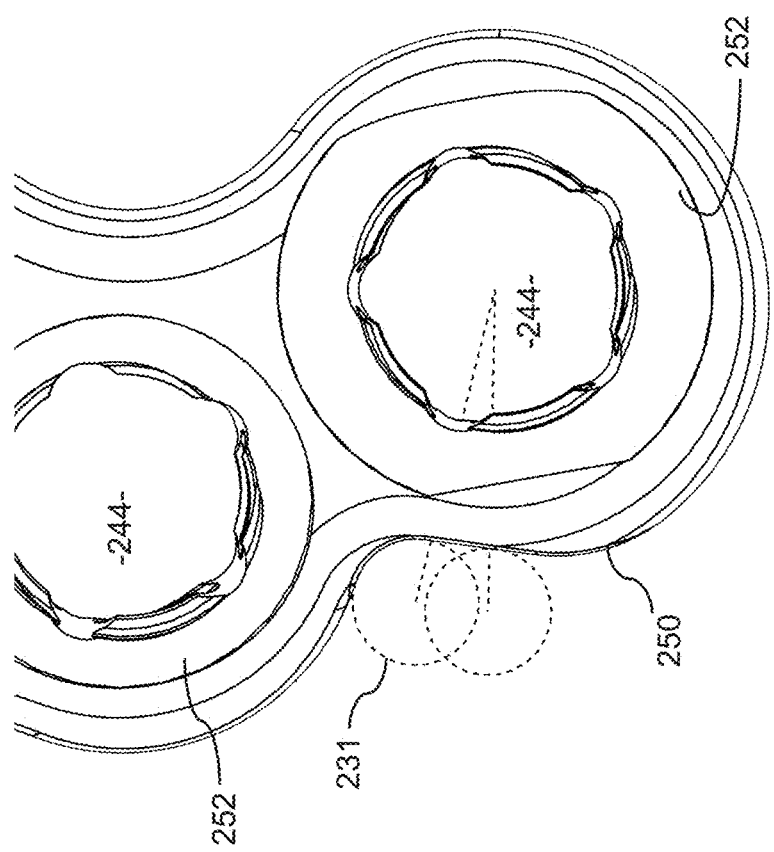
FIG. 29 is a top detail of the implant of 24 illustrating the contour of the keyed edge guide area.
Figure 30:
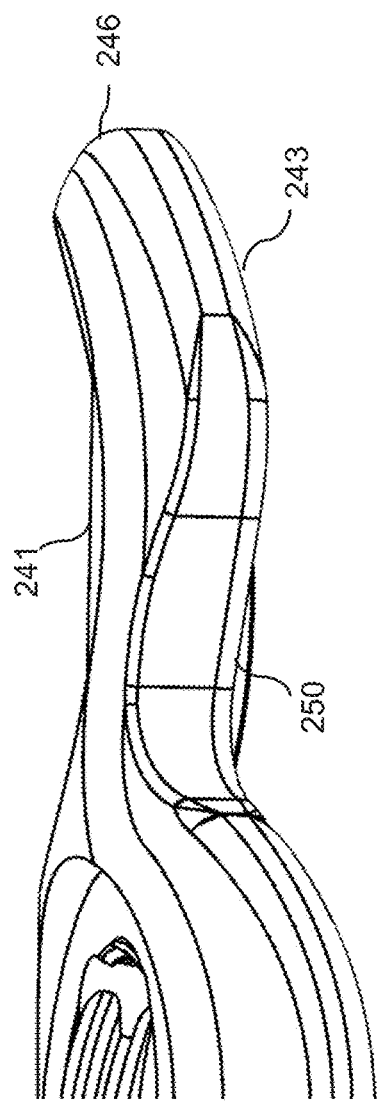
FIG. 30 is a side detail view of the keyed edge area of FIG. 29.

A third embodiment of the invention is shown in FIGS. 24-30. In this embodiment, the implant 240 has a top surface 241 and a bottom surface 243 separated by an edge 246 and the top surface 241 includes an edge 246 that provides the vertical edge key 250 for the post 231 of the drill guide rider 224. In this embodiment, the drill guide 220 has a drill guide body 222 with an arm 223 that carries the cannula housing 262 or which provides a two position drillway 266. An associated pointer 229 shows the position relative to a marker 232 on the plate surface. The drill guide body 222 has an annular surface which rotates in the counterbore 252 provided around a fastener recess 244. A set screw 219 secures the drill guide to the implant 240. FIGS. 29 and 30 illustrate the stable and controlled pivoting of the drill guide post 231 relative to the implant keyway 250.

A surgical technique in accordance with the invention is described as follows:

Step 1: Prepare the area for the plate and for fusion.
Step 2: Secure the drill guide to the plate.
Step 3: Place the plate and drill guide assembly and secure to the bone with one fastener through a fastener hole distal to the fusion and one fastener through the proximal end of the slot.
Step 4: Loosen and tighten the set screw as necessary to adjust and secure the drill guide assembly to provide for the desired positioning of the cannula members using the drill guide pointer and indicia on the plate.
Step 5: Drill the pilot holes or insert guide-wires for the independent fusion screws and place k-wires in the holes to verify the position.
Step 6: Following fluoroscopic verification of the k-wire position, remove the drill guide and place the compression screws as desired;
Step 7: Fill the remaining fastener holes with fasteners and close the incision While in accordance with the patent statutes the best mode and preferred embodiment have been set forth, the scope of the invention is not limited thereto, but rather by the scope of the attached claims.

What is claimed is:

1. A drill guide system for implanting a screw in bone comprising:
   an implant having a bone facing surface and an opposing top surface and defining a thickness between the bone facing surface and the top surface and first and second edge implant surfaces extending in parallel directions which are spaced apart; and
   a drill guide comprising a tether, an arm, and a rider, the tether having a tether surface that cooperates with the first edge implant surface so as to secure the drill guide on the implant while allowing the drill guide to pivot on a path relative to the top surface of the implant and the rider having a rider surface that cooperates with the second edge implant surface so as to define the path of pivoting for the drill guide on the implant and the arm having a drill guide cannula that defines an angle of entry for the screw which can be selected by pivoting the drill guide relative to the implant.

2. The drill guide system as set forth in claim 1, wherein the implant top surface includes a counterbore and the tether is a guide body and the tether surface is a bearing surface that cooperates with the counterbore.

3. The drill guide system as set forth in claim 2, wherein the counterbore is peripheral to a fastener opening in the implant.

4. The drill guide system as set forth in claim 3, wherein the drill guide rider is a post.

5. The drill guide system as set forth in claim 4, wherein the second edge implant surface is a key formed on a peripheral edge surface of the implant.

6. The drill guide system as set forth in claim 5, wherein the arm includes a pointer that indicates an angular position of the drill guide cannula.

7. The drill guide system as set forth in claim 6, wherein the top surface of the implant includes a mark to identify a position of the pointer.

8. The drill guide system as set forth in claim 7, wherein the arm includes a cannula housing which holds a cannula member to define the drill guide cannula.

9. The drill guide system as set forth in claim 8, wherein the cannula member can be positioned in the cannula housing to allow a selection of a depth of the drill guide cannula.

10. The drill guide system as set forth in claim 1, wherein the second edge implant surface is formed in a slot in the implant.

11. A drill guide system for implanting a screw in bone comprising:
    an implant having a bone facing surface and an opposing top surface and defining a thickness between the bone facing surface and the top surface, first and second edge implant surfaces extending in a direction of the thickness and which are spaced apart, and an implant rider surface; and
    a drill guide comprising a drill guide body having an axis and a bearing surface that cooperates with one of the first and second edge implant surfaces of the implant to permit the drill guide body to rotate about the axis, an arm which includes a drill guide cannula, and a rider, the rider having a rider surface that cooperates with the implant rider surface so as to secure the drill guide on the implant while allowing the drill guide to rotate, and the drill guide cannula defines an adjustable angle of entry for the screw which can be selected by pivoting the drill guide relative to the implant.

12. The drill guide system as set forth in claim 11, wherein the first edge implant surface is concentric with a fastener hole in the implant.

13. The drill guide system as set forth in claim 12, wherein the second edge implant surface is on a perimeter of the implant.

14. The drill guide surface as set forth in claim 11, wherein at least one of the first and second edge implant surfaces extends through the thickness of the implant.

15. A method of enabling a fusion surgery comprising providing a fusion implant system including an implant having a bone facing surface and an opposing top surface and defining a thickness between the bone facing surface and the top surface and first and second edge implant surfaces extending in a direction of the thickness and which are spaced apart; and
  using a drill guide with the implant, the drill guide comprising a drill guide body having an axis and a bearing surface that cooperates with one of the first and second edge implant surfaces of the implant to permit the drill guide body to rotate about the axis, an arm which includes a drill guide cannula, and a rider, the rider having a rider surface that cooperates with the other of the first and second edge implant surfaces so as to secure the drill guide on the implant while allowing the drill guide to rotate, and the drill guide cannula defines an adjustable angle of entry for a fusion screw which can be selected by pivoting the drill guide relative to the implant.

16. The method of enabling a fusion surgery as set forth in claim 15, wherein the implant is a plate and the other of the first and second edge implant surfaces is a vertical surface of the plate, the method including the step of using the vertical surface of the plate to guide the drill guide rider.

17. The method of enabling a fusion surgery as set forth in claim 16, including the step of placing a second fusion screw with a second drill guide and wherein the second drill guide has an attachment to avoid impingement with the fusion screw.

18. The method of enabling a fusion surgery as set forth in claim 17, wherein the second fusion screw is not parallel to the fusion screw.

19. The method of enabling a fusion surgery as set forth in claim 15, wherein the fusion implant system further includes one or more implant locking screws and wherein the arm avoids impingement of the fusion screw with the one or more implant locking screws.

* * * * *